(12) United States Patent
Gwenin et al.

(10) Patent No.: US 9,945,852 B2
(45) Date of Patent: Apr. 17, 2018

(54) METHOD FOR DETERMINING THE PRESENCE OR ABSENCE OF A BIOMARKER

(75) Inventors: Christopher David Gwenin, Gwynedd (GB); Mark Stephen Baird, Gwynedd (GB); Vanessa Valerie Gwenin, Gwynedd (GB); Mark Pitts, Gwynedd (GB)

(73) Assignee: Arcis Biotechnology Holdings Limited, Warrington (GB)

( * ) Notice: Subject to any disclaimer, the term of this patent is extended or adjusted under 35 U.S.C. 154(b) by 520 days.

(21) Appl. No.: 14/115,929

(22) PCT Filed: May 4, 2012

(86) PCT No.: PCT/GB2012/050978
§ 371 (c)(1),
(2), (4) Date: Dec. 16, 2013

(87) PCT Pub. No.: WO2012/153111
PCT Pub. Date: Nov. 15, 2012

(65) Prior Publication Data
US 2014/0127709 A1    May 8, 2014

(30) Foreign Application Priority Data
May 6, 2011 (GB) .................. 1107557.9

(51) Int. Cl.
| G01N 33/569 | (2006.01) |
| C07H 13/04 | (2006.01) |
| C07C 321/06 | (2006.01) |
| G01N 33/58 | (2006.01) |

(52) U.S. Cl.
CPC ....... *G01N 33/5695* (2013.01); *C07C 321/06* (2013.01); *C07H 13/04* (2013.01); *G01N 33/585* (2013.01)

(58) Field of Classification Search
None
See application file for complete search history.

(56) References Cited

U.S. PATENT DOCUMENTS

| 6,526,828 B1 * | 3/2003 | Dayan ..................... G01G 3/13 73/24.01 |
| 6,699,507 B1 * | 3/2004 | Albrecht .......... A61K 47/48861 424/489 |
| 2006/0057621 A1 * | 3/2006 | Lyashchenko ..... G01N 33/5695 435/6.15 |

FOREIGN PATENT DOCUMENTS

| WO | 2009130506 A2 | 10/2009 |
| WO | 2009130508 A1 | 10/2009 |
| WO | 2010086667 A2 | 8/2010 |

OTHER PUBLICATIONS

Rosi et al., "Nanostructures in Biodiagnostics," Chem. Rev., 2005, vol. 105, No. 4, pp. 1547-1562.*
Koza et al., "The synthesis of single enantiomers of mycobacterial ketomycolic acids containing cis-cyclopropanes," 2009, pp. 10214-10229, Tetrahedron, vol. 65, Elsevier.
Al Dulayymi et al., "The first syntheses of single enantiomers of the major methoxymycolic acid of*Mycobacterium tuberculosis*," 2006, pp. 2571-2592, Tetrahedron, vol. 63, www.sciencedirect.com.
Patent Cooperation Treaty, Preliminary Report on Patentability and Written Opinion for PCT/GB2012/050978 dated Nov. 12, 2013, 8 pages.
Patent Cooperation Treaty, International Search Report for PCT/GB2012/050978 dated Aug. 21, 2012, 5 pages.
Patent Cooperation Treaty, Written Opinion for the International Searching Authority for PCT/GB2012/050978 dated 21 2012, 6 pages.
Ozoemena et al., "Electron transfer dynamics across self-assembled N-(2-mercaptoethyl) octadecanamide/mycolic acid layers: impedimetric insights into the structural integrity and interaction with anti-mycolic acid antibodies," 2010, pp. 345-357, Physical Chemistry Chemical Physics Royal Society of Chemistry, vol. 12, No. 2 (XP002682088).
Lemmer et al., "Detection of Antimycolic Acid Antibodies by Liposomal Biosensors," 2009, pp. 79-104, Methods in Enzymology, vol. 464 (XP008145177).
Driver, "Synthesis of a thiolated mycolic motif for the development of novel TB diagnostics," 2011, 1 page, retrieved from internet: www.netd.ac.za/?action=view&identifier=aoi:UP:etd-06092009-191707 (XP002682089).
Hasegawa, "Structural Analysis of Biological Aliphatic Compounds Using Surface-Enhanced Fourier Transform Raman Spectroscopy," 2004, pp. 457-462, Biopolymers, vol. 73, No. 4 (XP002682090).
Liu et al., "Single chain fragment variable recombinant antibody functionalized gold nanoparticles for a highly sensitive colorimetric immunoassay," 2009, pp. 2853-2857, Biosensors and Bioelectronics, vol. 24, No. 9 (XP026053077).
Chakraborty et al., "A rapid immunochromatographic assay for the detection of *Mycobacterium tuberculosis* antigens in pulmonary samples from HIV seropositive patients and its comparison with conventional methods," 2009, pabes 12-17, Journal of Microbiological Methods, vol. 76, No. 1 (XP025780010).

* cited by examiner

*Primary Examiner* — Galina Yakovleva
(74) *Attorney, Agent, or Firm* — Hoffman Warnick LLC

(57) ABSTRACT

A method of determining the presence or absence in a sample of a biomarker, the method comprising: (a) linking an antigen to colloidal gold to provide a gold-antigen species; (b) contacting the gold-antigen species with the sample; (c) adding a diagnosis agent to the sample; and (d) observing the color of the sample.

8 Claims, No Drawings

METHOD FOR DETERMINING THE PRESENCE OR ABSENCE OF A BIOMARKER

The present invention relates to a kit and method for detecting an antibody in a sample. In particular the invention provides a quick method for determining whether or not an individual is infected with a mycobacterial disease.

Pathogenic and non-pathogenic mycobacteria are very widespread in the environment and their rapid detection and distinction represents an important public health target.

For example, tuberculosis is a serious and often fatal disease which affects humans and other animals and is caused by infection with mycobacteria. Infection with *Mycobacterium tuberculosis* is very common and it is estimated that up to a third of the world's population is infected with the bacterium. Most of those infected will never develop the active disease but because it is often fatal if left untreated, early diagnosis of the disease is essential. Methods of detecting *M. tuberculosis* are known but these existing methods have a number of disadvantages. It can often take a long time for the results of a test to be known, the equipment needed is expensive or difficult to use and the results are not always reliable. A number of serodiagnostic assays have been developed for the diagnosis of tuberculosis but none of these have been assessed as reaching the standards required by the World Health Organisation.

Incidence of active tuberculosis disease is very common in certain areas of the world, especially where there is co-infection with HIV. The presence of HIV can suppress some of the indicators typically found in a patient infected with *M. tuberculosis*, leading to missed diagnoses.

The life expectancy of an individual co-infected with *M. tuberculosis* and HIV is often only a few weeks. Thus there exists an urgent need to provide a method by which infection with tuberculosis and other mycobacterial diseases can be detected quickly and reliably.

Infectious diseases, for example tuberculosis, can cause a person or animal infected with the disease to produce antibodies. Identification of these antibodies in a sample taken from an infected individual can lead to a diagnosis of the disease.

According to a first aspect of the present invention there is provided a method of determining the presence or absence in a sample of a biomarker, the method comprising:
(a) linking an antigen to colloidal gold to provide a gold-antigen species;
(b) contacting the gold-antigen species with the sample;
(c) adding a diagnosis agent to the sample; and
(d) observing the colour of the sample.

The first aspect of the invention relates to a method of detecting a biomarker. A biomarker as used herein refers to a molecule produced by a living organism which is characteristic of a particular condition. The biomarker may be a molecule which is produced when the organism has a particular disease and/or when the organism has been exposed to a pathogen. In some preferred embodiments the biomarker is a molecule which is produced when an organism has been infected with a pathogenic disease. Such a disease may be caused by infection for example with bacteria, viruses or fungi.

In some embodiments the biomarker may be a molecule which is characteristic of a non-pathogenic condition, for example an auto-immune disease.

In preferred embodiments the present invention involves a method of determining the presence or absence of a biomarker indicative of exposure to mycobacteria or related species that produce analogues of mycolic acid, for example corynobacteria.

In preferred embodiments, the present invention relates to a method of determining the presence or absence in a sample of a biomarker indicative of exposure to mycobacteria. By this we mean to refer to any molecule or combination of molecules that would be produced by an organism in response to exposure to mycobacteria. The organism may be a plant or animal. Preferably it is an animal. Most preferably the sample donor is a mammal.

The method of the present invention may be used to determine the presence or absence of a biomarker indicative of exposure to non-pathogenic or environmental mycobacteria. However in preferred embodiments the biomarker is indicative of infection with a mycobacterial disease. In such embodiments the biomarker is an antibody indicative of infection with the disease and may be further referred to herein as a "disease antibody".

The present invention therefore preferably relates to a method of determining the presence or absence in a sample of a disease antibody indicative of infection with a mycobacterial disease. The term "disease antibody" as used herein refers to an antibody produced by an individual infected with a disease.

The present invention may be used to determine the presence or absence of a disease antibody indicative of infection with any disease caused by infection with mycobacteria. Examples of such diseases include tuberculosis, leprosy, pulmonary disease, burili ulcer and bovine tuberculosis.

The present invention may also be used to determine the presence or absence of antibodies to lipids generated by exposure to non-pathogenic mycobacteria.

The invention finds particular utility in determining the presence or absence in a sample of disease antibodies indicative of the presence of tuberculosis. The sample may be taken from any animal suspected of infection with tuberculosis. Suitably the animal is a human.

Tuberculosis is a disease which is particularly prevalent in developing countries and many sufferers are also infected with HIV. However some of the current techniques used in the diagnosis of tuberculosis rely on the detection of a protein antibody. Antibodies against proteins may be suppressed in individuals who are HIV-positive.

Step (a) of the present invention involves linking an antigen to colloidal gold to provide a gold-antigen species.

Preferably the antigen is a mycolic acid derived antigen. Such compounds are antigens for lipid antibodies generated by infection with mycobacteria. This is highly advantageous since, unlike protein antibodies, antibodies against lipids (which may be referred to herein as lipid antibodies) are not suppressed in individuals with compromised immune systems, for example those infected with HIV.

The "mycolic acid derived antigen" may be selected from one or more of the following classes of compounds:
(i) mycolic acids obtained from natural sources;
(ii) synthetically prepared mycolic acids;
(iii) salts of mycolic acids;
(iv) esters of mycolic acids (i) and/or (ii);
(v) sulfur-containing mycolic acids and/or salts or esters thereof;
(vi) simple structural analogues of mycolic acids and/or salts or esters thereof.

Mycolic acids obtained from natural sources (i) are typically available as mixtures. These typically contain different classes of mycolic acids and each class will usually contain a mixture of different homologues.

It is highly advantageous to use synthetically prepared mycolic acids (ii) since these are available as single compounds in high purity (for example greater than 95% or greater than 99%). The use of single compounds allows greater substrate selectively to be achieved.

Salts of natural mycolic acids and/or synthetic mycolic acids may be useful. Suitable salts include ammonium, alkali metal and alkaline earth metal salts, for example salts of lithium, potassium, sodium, calcium or barium.

Suitable esters (iv) for use as antigens include glycerol esters and especially sugar esters. Preferred sugar esters of mycolic acids are trehalose monomycolates or trehalose dimycolates (also known as cord factors). Cord factors can be isolated as mixtures from natural sources. Esters of mycolic acids for use herein as antigens may be synthetically prepared. They may be prepared by esterification of synthetically prepared mycolic acids or by esterification of mycolic acids isolated from natural sources.

By sulfur-containing mycolic acids and/or esters or salts thereof we mean to refer to synthetic compounds which are analogues of natural mycolic acid compounds rather than naturally occurring compounds that contain sulfur. Suitable sulfur-containing mycolic acid derivatives (v) may include any compound in which one or more carbon atoms and/or one or more oxygen atoms of a mycolic acid derived compound has been replaced by a sulphur atom. sulfur-containing mycolic acid derivatives also include compounds in which a hydrogen substituent has been replaced with a moiety "SX" wherein hydrogen, $SR^1$ or $COR^2$ in which $R^1$ is an optionally substituted alkyl, alkenyl, acyl or aryl group and $R^2$ is an optionally substituted alkyl, alkenyl or aryl group. Sulfur-containing antigens (v) include many novel compounds and are further discussed herein in relation to the second aspect of the invention.

Simple structural analogues of mycolic acids and/or esters or salts thereof (vi) which maybe used herein as antigens include compounds which include fewer functional groups and/or stereocentres than are found in natural mycolic acid compounds but have many structural features in common, for example they include a similar number of carbon atoms and have a simpler substitution pattern.

Suitable synthetically prepared mycolic acid derived compounds for use herein as antigens include the mycolic acid compounds described in WO2009/130506, WO2009/130508 and the sugar esters described in WO 2010/086667.

As is shown by way of example in formula I, two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in formula I), can be differently substituted in both the proximal (the one nearer the hydroxy-acid) and the distal position (further from the carboxylic acid).

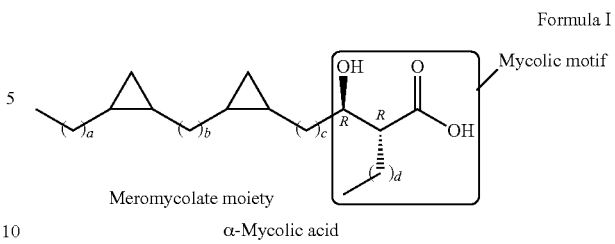

Formula I

Meromycolate moiety

α-Mycolic acid

The mycolic acids are broadly separated into classes, according to the groups present in the meromycolate moiety. The proximal or distal functional groups can include cyclopropanes, double bonds, an epoxy group, a methoxy group, carbonyl group, carboxyl group or methyl group.

Suitable mycolic acid classes for use herein as antigens include keto mycolic acids having the structure shown in formula IIa; hydroxy mycolic acids having the structure shown in formula IIb; alpha mycolic acids having the structure shown in formula IIc; and methoxy mycolic acids having the structure shown in formula IId:

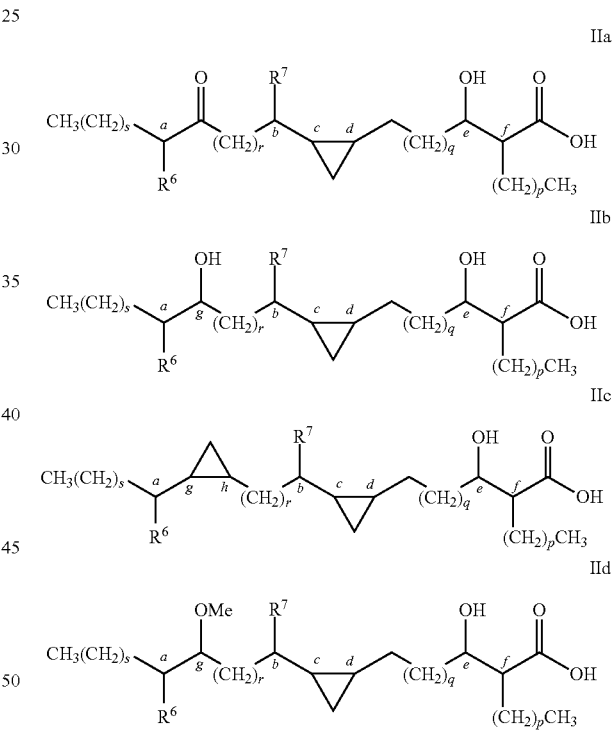

In each of the structures IIa, IIb, IIc and IId $R^6$ may be hydrogen or $C_1$ to $C_4$ alkyl. Preferably $R^6$ is hydrogen or methyl.

In each of the structures IIa, IIb, IIc and IId $R^7$ may be hydrogen or $C_1$ to $C_4$ alkyl. Preferably $R^7$ is hydrogen or methyl.

In each of the structures IIa, IIb, IIc and IId p is preferably from 4 to 40, preferably from 8 to 36, more preferably from 12 to 32, for example from 16 to 30, more preferably from 20 to 28, for example from 22 to 26.

In the structures IIa, IIb, IIc and IId q is preferably from 2 to 40, more preferably from 4 to 36, for example from 6 to 30, preferably from 8 to 24, for example from 10 to 20 and preferably from 12 to 18.

In the structures IIa, IIb, IIc and IId, r is preferably from 2 to 40, for example from 6 to 36, preferably from 10 to 32, for example from 12 to 28, and preferably from 14 to 24.

In the structures IIa, IIb, IIc and IId, s is preferably from 2 to 40, for example from 6 to 36, preferably from 10 to 32, for example from 12 to 28, and preferably from 14 to 24.

In the structures IIa, IIb, IIc and IId, each of the chiral centres indicated at a, b, c, d, e, f, g and h may independently have either an (R) or an (S) configuration. Each cyclopropyl group may have either absolute stereochemistry and may have a trans or a cis configuration.

Any of the stereocentres indicated by a, b, c, d, e, f, g or h may be racemic. In the case of structure IIa it is possible that the stereocentre designated a will be racemic as this is a readily epimerisable position.

In addition to the compounds illustrated by the structures IIa, IIb, IIc and IId, other classes of mycolic acids may be useful as antigens in the present invention. Further suitable classes of mycolic acid include those substituted with epoxy and alkene groups in the meromycolate moiety. The structure of such compounds will be known to the person skilled in the art. Each of the above-described mycolic acid compounds may be used as single compounds prepared synthetically and/or may be included in mixtures of synthetic compounds and/or may be included in mixtures isolated from natural sources. Any of these compounds could be used in the preparation of synthetic esters or be present in naturally occurring cord factors.

Especially preferred esters (iv) for use as antigens are sugar esters, especially trehalose monomycolates and trehalose dimycolates. Trehalose dimycolates (or cord factors) have the structure shown in formula III wherein MA represents the residue of a mycolic acid:

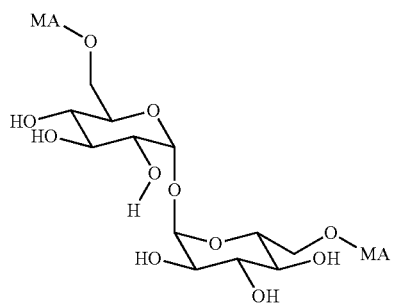

Formula III

In formula III each MA residue may be of the same or a different mycolic acid.

In some embodiments the antigen comprises a keto mycolic acid or a derivative thereof.

In some embodiments the antigen comprises a hydroxy mycolic acid or a derivative thereof.

In some embodiments the antigen comprises a methoxy mycolic acid or a derivative thereof.

In some embodiments the antigen comprises an alpha mycolic acid or a derivative thereof.

Examples of suitable compounds which may be used as antigens in the present invention either alone or in combination are shown in formula IV:

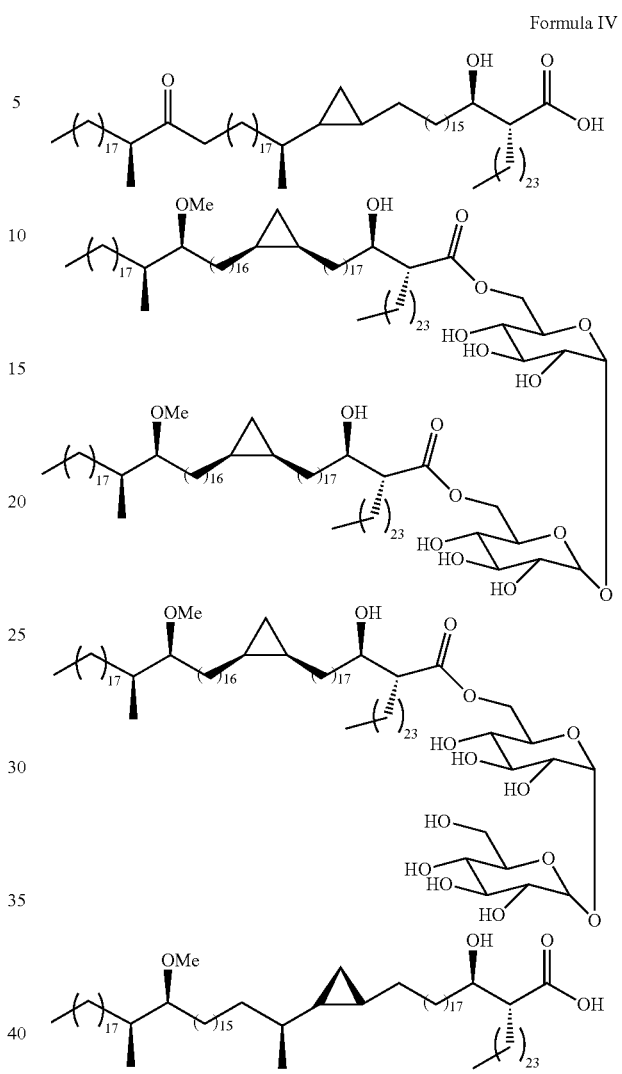

Formula IV

Simple structural analogues of mycolic acids (vii) which can be used herein as antigens include compounds having the structures indicated in formula IIa, IIb, IIc or IId in which some or all of the stereocentres a, b, c, d, e, f, g and h are racemic and in which $R^6$ and $R^7$ may each be hydrogen.

Simple structural analogues of cord factors include compounds having the structure indicated in formula III wherein one or each MA group is a simple analogue as described above or in which one or each MA is a fatty acid having a long carbon chain.

In step (a) of the method of the present invention an antigen is linked to colloidal gold. Suitably the antigen is linked to the gold by a gold-sulfur bond.

In some embodiments the antigen may be directly bonded to the colloidal gold by a sulfur atom contained within the antigen molecule.

In some embodiments the antigen may be linked to the colloidal gold via a sulfur-containing linker compound. Such a sulfur-containing linker compound suitably forms a sulfur-gold bond with the colloidal gold and forms an interaction with the antigen.

The interaction formed between the antigen and the sulfur-containing linker compound may be a covalent bond, an electrostatic interaction, an ionic interaction, a hydrophobic interaction, a hydrogen bond or a mixture thereof.

Any suitable compound able to form an interaction with the antigen and a sulfur-gold bond may be used as the sulfur-containing linker compound.

Suitable sulfur-containing linker compounds include a functional group which is able to form a gold-sulfur bond, for example a thiol, a disulfide or a thioester.

Some preferred sulfur-containing linker compounds for use herein include simple long-chain thiol molecules, for example thio-alkanes or thio-alkenes. Preferred such compounds are preferably thioalkanes including from 4 to 40, preferably 8 to 36 carbon atoms and having a terminal SH group. The thiol moiety is able to bond to the gold and the alkyl chain is able to form a hydrophobic interaction with a hydrophobic portion of the mycolic acid.

Some preferred sulfur-containing linker compounds for use herein include fatty acid derivatives. In such compounds, the sulfur moiety may be located along the fatty carbon chain, suitably at the end of the chain, or may be bonded to the acid moiety. Preferably the sulfur-substituent is bonded to the acid moiety.

Suitable fatty acid derivatives include compounds of formula HSRCOOH in which R is an optionally substituted alkylene or alkenylene chain having form 4 to 32, preferably 8 to 26, more preferably 12 to 24 carbon atoms.

Preferred sulfur-substituted fatty acids include compounds of formula RCOXSH in which R is an optionally substituted alkyl or alkenyl group having from 4 to 32, preferably from 8 to 26, more preferably from 12 to 22 carbon atoms and X is a connecting group. Preferably R is an alkyl chain. X may be any group able to bond to a carbonyl group and a thiol. Preferably X is an alcohol or amine, suitably $O(CH_2)_n$ or $N(CH_2)_n$ wherein n is from 1 to 10, suitably from 1 to 5, for example 2 or 3. One especially preferred sulfur-containing linker compound for use herein is $CH_3(CH_2)_{16}CONCH_2CH_2SH$.

Suitably in preferred embodiments in which the sulfur-containing linker compound has the formula RCOXSH and the antigen is a mycolic acid derived antigen, a gold-sulfur bond is formed between the thiol-substituted acid group and there is a hydrophobic interaction between the fatty chain R and the mycolic acid derived antigen. Without wishing to be bound by theory it is believed that the hydrophobic chain at the α position of the mycolic motif binds to the fatty chain R of the sulfur-containing linker compound leaving the meromycolate moiety free to interact with the biomarker.

In an alternative embodiment in which the sulfur substituent is on the fatty chain, this may form a bond with the gold and the carboxylic acid moiety may then form an interaction with a hydrophilic portion of the mycolic acid derived antigen. This interaction may be an electrostatic interaction, a hydrogen bond or a covalent bond. The hydrophilic portion of the mycolic acid derived antigen may be the hydroxy, alkoxy, keto, epoxy or acid functionality of a mycolic acid or the sugar residue of a sugar ester.

In embodiments in which a mycolic acid derived antigen is directly bonded to the colloidal gold by a sulfur atom contained within the antigen molecule such molecules are novel compounds. According to a second aspect of the present invention there is provided a compound having a structure based on a mycolic acid or an ester thereof which contains at least one sulfur atom.

In preferred embodiments the compounds of the second aspect are of formula V:

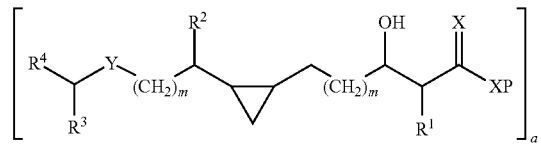

(V)

wherein each X may be independently O, $NR^{10}$ or S; P is hydrogen, a sugar residue, $SR^8$, $COR^9$ or $R^{11}SR^7$; a is 1 or 2; $R^1$ is an optionally substituted alkyl or alkenyl group; n is from 0 to 40; $R^2$ is $SR^7$, methyl or hydrogen; m from 0 to 40; Y is selected from C=O, C—OMe, C-OEt, a cyclo propyl group, an epoxide group, C—OH, $R^5C$=$CR^6$ and $SR^7$; $R^3$ is $SR^7$, methyl or hydrogen; $R^4$ is an optionally substituted alkyl or alkenyl group; $R^5$ and $R^6$ is each independently hydrogen or an optionally substituted alkyl group; each $R^7$ is independently hydrogen, $SR^8$ or $COR^9$; each $R^8$ is independently an optionally substituted alkyl, alkenyl, aryl or acyl group; each $R^9$ is independently an optionally substituted alkyl, alkenyl or aryl group; each $R^{10}$ is independently hydrogen or an optionally substituted alkyl, alkenyl or aryl group; and $R^{11}$ is an optionally substituted alkylene, alkenylene or arylene group.

In some embodiments at least one X is S. In some embodiments each X is S. In preferred embodiments each X is O. In some embodiments one or more X is $NR^{10}$. In such embodiments $R^{10}$ is preferably hydrogen or a $C_1$ to $C_4$ alkyl group.

$R^1$ is an optionally substituted alkyl or alkenyl group. Suitably $R^1$ has from 4 to 40 carbon atoms, preferably from 8 to 36, preferably from 12 to 32, more preferably from 16 to 30, suitably form 20 to 28, for example from 22 to 26.

When $R^1$ is substituted it is preferably substituted with one or more thiol-substituents. Preferably $R^1$ is substituted with up to 6 thiol groups, preferably up to 4, preferably up to 2. Most preferably $R^1$ is substituted with a single thiol group.

Suitably the or each thiol substituent is located towards the end of the chain away from the acid group.

In some especially preferred embodiments $R^1$ is $(CH_2)_bSH$ wherein b is from 4 to 40, preferably 12 to 32, more preferably 20 to 28.

In some embodiments $R^1$ is an unsubstituted alkyl group.

Suitably n is from 2 to 40, preferably from 4 to 36, suitably from 6 to 30, preferably from 8 to 24, more preferably from 10 to 20, most preferably from 12 to 18.

$R^2$ may be $R^7$, Me or H. Preferably $R^2$ is Me or H. Most preferably $R^2$ is H.

Suitably m is from 2 to 40, preferably from 6 to 36, more preferably from 10 to 32, preferably from 12 to 28, most preferably from 14 to 24.

Y is selected from C=O, C—OMe, C-OEt, a cyclo propyl group, an epoxide group, C—OH, $R^5C$=$CR^6$ and $SR^7$.

When Y is cyclopropyl two atoms of the cyclopropyl group lie in the main carbon chain of the meromycolate moiety. The cyclopropyl group may have a cis or a trans configuration. In some embodiments it has a cis configuration. In some embodiments it has a trans configuration.

When Y is epoxide the two carbon atoms of the epoxide group lie in the main carbon chain of the meromycolate moiety. The epoxide may have a cis or a trans configuration.

When Y is $R^5C$=$CR^6$ each of $R^5$ and $R^6$ may independently be hydrogen or an optionally substituted alkyl group.

Preferably each is hydrogen or an optionally substituted alkyl group. Preferably each is hydrogen or a $C_1$ to $C_4$ alkyl group. More preferably each of $R^5$ and $R^6$ is independently methyl or hydrogen. Preferably each is hydrogen. When Y is $R^5C=CR^6$ the double bond may have an E or a Z configuration.

$R^3$ may be $SR^7$, Me or H. Preferably $R^3$ is Me or H. Most preferably $R^3$ is H.

$R^4$ is an optionally substituted alkyl or alkenyl group. Preferably $R^4$ is an optionally substituted alkyl group. Suitably $R^4$ has from 2 to 40 carbon atoms, preferably 6 to 36, more preferably from 10 to 32, for example from 12 to 28 and most preferably from 14 to 24.

When $R^4$ is substituted it is preferably substituted with up to 6 thiol groups, preferably up to 4, more preferably up to 2. Suitably $R^4$ is substituted with a single thiol group. Suitably the or each thiol substituent when present is located towards the end of the chain, away from the acid group.

In some embodiments $R^4$ may be $HS(CH_2)_c$ wherein c is from 1 to 40, preferably from 8 to 32, for example from 14 to 24.

In some embodiments $R^4$ is an unsubstituted alkyl group.

P may be hydrogen, a sugar residue, $SR^8$ or $COR^9$. In some preferred embodiments P is hydrogen. When P is hydrogen, a is 1.

When P is a sugar residue, a may be 1 or 2. P may be any suitable sugar residue. Preferably P is a saccharide residue. P may be the residue of monosaccharide, a dissaccharide or an oligosaccharide. P may include any suitable saccharide unit. When P is a disaccharide or an oligosachamide each saccharide may be the same or different.

When a is 2 each P may be the same or different.

When P is a sugar residue the sugar residue may contain one or more sulfur atoms in place of one or more oxygen atoms.

In some preferred embodiments a is 1 and P is a trehalose residue and the compound of formula V is a sulfur-substituted trehalose monomycolate.

In some preferred embodiments, a is 2 and each P is a glucose derived moiety such that the two P groups are bonded to form a trehalose moiety. In such embodiments the compound is a sulfur-substituted trehalose dimycolate (or cord factor).

In some embodiments in which a is 1, P may be a sugar residue which is substituted with a fatty acid residue. This fatty acid residue may contain a sulfur-substituent.

P may only be $SR^8$ or $COR^9$ when the atom X directed bonded to P is S.

In some embodiments P is a group $XR^{11}SR^7$. In such embodiments a is suitably 1 and the X of the group XP is preferably O or $NR^{10}$. $R^{10}$ is preferably H. $R^{11}$ is preferably an alkylene, alkenylene or arylene group having 1 to 20, preferably 1 to 10, more preferably 1 to 6 carbon atoms. Preferably $R^{11}$ is phenylene or a $C_1$ to $C_4$ alkylene group, for example an ethylene or propylene group.

When any $R^7$ is H, the molecule includes a thiol moiety which is able to directly bond with the colloidal gold.

When $R^7$ is $SR^8$ the molecule includes a disulfide moiety. Such a functional group is able to form a gold-sulfur bond. $R^8$ is an optionally substituted alkyl, alkenyl, aryl or acyl group. Preferably $R^8$ is an alkyl or aryl group, preferably an unsubstituted $C_1$ to $C_4$ alkyl group or a phenyl group.

When $R^7$ is $COR^9$ the molecule includes a thioester moiety. Such a functional group is able to form a gold-sulfur bond. $R^9$ is independently an optionally substituted alkyl, alkenyl or aryl group. Preferably $R^9$ is an alkyl or aryl group, preferably an unsubstituted $C_1$ to $C_4$ alkyl group or a phenyl group.

Step (a) of the method of the present invention involves linking an antigen with colloidal gold. This may be carried out by any suitable means and suitably involves the formation of a gold-sulfur bond. In embodiments in which the antigen includes a sulfur substituent step (a) suitably involves mixing the antigen and colloidal gold in a suitable solvent. A suitable illustrative method is described in example 16. Modifications to the method could be made or alternative methods used as will be appreciated by the person skilled in the art.

In embodiments in which a sulfur-containing linker compound is used step (a) suitably involves mixing the linker compound with colloidal gold in a suitable solvent and subsequently adding the antigen. A suitable illustrative method is described in example 17. The skilled person will appreciate that such a method can be modified or an alternative method may be used.

In step (b) of the method of the present invention the gold-antigen species is contacted with the sample.

This typically involves contacting a suspension of the gold-antigen species with the sample. The sample may be diluted with a suitable solvent if appropriate. The gold-antigen species may be suspended in any suitable solvent. Preferably it is suspended in an aqueous solvent. This solvent may contain other dissolved species. One suitable solvent is a phosphate buffer.

Any suitable sample may be analysed using the present invention. Suitably the sample is selected from serum, blood, saliva, urine or sputum. In embodiments in which the sample is whole blood the method may include a step of first separating serum from the blood. This may be achieved, for example, by providing a filter through which the blood must first flow before it reaches the gold-antigen species. Other suitable methods will be known to the person skilled in the art.

When the gold-antigen species is contacted with a sample which contains a biomarker this biomarker becomes bound to or interacts with the mycolic acid derived antigen.

After the sample has been contacted with a suspension of the gold-antigen species the resultant mixture is preferably a suspension.

Step (c) involves adding a diagnosis agent to the sample. Preferably step (c) is carried out after step (b).

Thus in preferred embodiments step (c) involves adding a diagnosis agent to a mixture comprising a gold-antigen species and the sample. Any suitable diagnosis agent may be used. A diagnosis agent is preferably a chemical species which when contacted with a mixture containing a gold-antigen species and a sample produces a different effect depending on whether the sample contains or does not contain the biomarker. Preferably the different effect is a different colour.

Preferably the diagnosis agent is an aqueous composition. Preferably it has dissolved therein one or more salts. Suitable diagnosis agents include saturated solutions of alkali metal and alkaline earth metal salts, for example magnesium chloride, potassium chloride and sodium chloride. In preferred embodiments the diagnosis agent is a saturated sodium chloride solution.

Step (d) involves observing the colour of the sample. This is the colour of the sample/gold-antigen mixture following addition of the diagnosis agent.

When the gold-antigen species is contacted with a sample containing biomarker this becomes bound to the antigen.

When no biomarker is present the gold-antigen species remains unbound in an aqueous colloidal suspension. When a saturated sodium chloride solution is used as the diagnosis agent, addition to the sample mixture causes a colour change. Without wishing to be bound by theory it is believed that this colour change is due to aggregation and/or precipitation of the unbound-antigen species. When saturated sodium chloride solution is added to a sample mixture in which a biomarker is bound to the gold-antigen species, this biomarker-antigen-gold complex is stable at high salt concentrations. Thus no precipitation/aggregation is believed to occur and no colour change results.

Thus when saturated sodium chloride solution is used as a diagnosis agent, if a colour change is observed in step (d) this is an indication that the sample does not contain the biomarker (a negative sample). If no colour change is observed in step (d) this is an indication that the sample does contain a biomarker (a positive sample).

However embodiments in which a different diagnosis agent is used may give different results. Thus in some embodiments a positive sample may cause a colour change and a negative sample may cause no colour change. In some embodiments a positive sample may cause a different colour change to that observed with a negative sample.

In some embodiments step (d) may involve quantitatively measuring the colour change. Quantitative analysis of this type may also help determine the severity of infection with a mycobacterial disease.

Step (d) may also involve measuring the colour change over time. This information may also be useful in determining the type or extent of infection with a mycobacterial disease.

In some embodiments step (d) may involve simply visually observing the presence or absence of a colour change to provide a qualitative assessment. In other embodiments step (d) may involve quantitative measurement of the intensity of light absorbance at one or more wavelengths and at one or more points in time. In some embodiments the intensity of the light absorbance may be measured continuously over a period of time. Thus step (d) of the method of present invention may involve measuring the change of colour with time.

One method by which a quantitative measure of precipitation/aggregation of colloidal gold may be measured is described in example 18.

Quantitative measurement of the intensity of visible light may be carried out by any suitable means, including, for example a UV-visible spectrometer.

Suitably where the intensity of visible light is quantitatively measured at one or more points in time and at one or more wavelengths this data may be recorded using a computer. Such a computer could then be used to compare new samples with data from previous samples to increase the accuracy and specificity of identification of particular antibody combinations indicative of infection with a mycobacterial disease.

However a particular advantage of the present invention is that it enables a very quick, simple test to be carried out to determine whether or not a particular sample contains a biomarker indicative of exposure to mycobacteria for example a disease antibody indicative of infection with a mycobacterial disease. Contacting the sample with a gold-antigen species and adding a diagnosis agent can be carried out at remote locations. The colour change can be observed straight away providing an immediate indication whether the provider of the sample is infected with a mycobacterial disease.

According to a third aspect of the present invention there is provided a kit for testing for the presence or absence of a biomarker, the kit comprising a container comprising a gold-antigen species and a diagnosis agent wherein the gold-antigen species comprises an antigen linked to colloidal gold.

Preferred features of the third aspect are, where appropriate, as defined in relation to the first and/or second aspects. In the kit of the present invention the gold-antigen species may be provided in solid form to be diluted shortly before use. A suitable diluent (for example a phosphate buffer) may also be provided in the kit. The container is preferably one to which the sample and diagnosis agent could be added. Preferably it is selected to allow a colour change to be observed easily. The kit may also include a second container containing a gold-antigen species to be used as a control.

Preferably the antigens provided in the kit are one or more mycolic acid derived antigens. These mycolic acid derived antigens are suitably selected according to the particular biomarker for which the kit is intended to detect. In some embodiments the kit may comprise a plurality of containers each containing a gold-antigen species which includes a different mycolic acid derived antigen. Each different antigen may be used to test for the same or a different disease. The diagnosis of some diseases, for example, may require confirming the presence of a combination of different disease antibodies.

It is highly advantageous to include synthetic antigens as these can be provided in high purity. In some parts of the world exposure to mycobacteria is very common and thus many humans and other animals living in these areas will produce antibodies to mycobacterial antigens even if they are not infected with an active disease, for example active tuberculosis. This can lead to difficulty in providing a positive diagnosis of a particular disease. The present invention allows the response to single antigens and particular defined combinations thereof to be determined and if necessary in a quantitative manner. It therefore provides a more reliable and accurate assessment of the presence or absence of specific disease antibodies known to be indicators of infection with a mycobacterial disease.

A particular advantage of the method of the present invention is that it can provide a result on a very short timescale. A sample may be contacted with the gold-antigen species for only 5 minutes before adding the diagnosis agent. This leads to an observable colour change straight away which indicates whether a sample is positive or negative for a particular biomarker.

When used to analyse known samples of sera from individuals some of whom had been infected with *M. tuberculosis*, the method of the present invention was found to provide a greater degree of discrimination between positive and negative samples compared with using standard methods based on ELISA assays.

When the method of the present invention is used to test for disease antibodies indicative of infection with a mycobacterial disease it can provide results very quickly, with improved accuracy and at relatively low cost. It therefore provides significant advantages over the prior art.

The invention will now be further described with reference to the following non-limiting examples.

EXAMPLE 1

Compound A was prepared as follows:

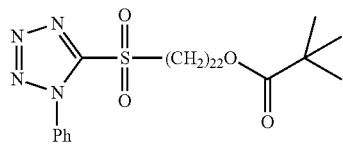

A 2,2-dimethylpropinic acid 12-(phenyl-1-H-tetrazole-5-yl-sulfonyl)-dodecyl ester was prepared using a method analogous to that described by Al Dulayymi, Baird, Roberts, Verschoor and Deysel in supplementary information to Tetrahedron 2007, 63, 2571-2592.

Sodium bis(trimethylsilyl) amide (70 ml, 74.6 mmol) was added dropwise to a stirred solution of 10-bromodecanal (9 g, 38.2 mmol) and 2,2-dimethylpropinic acid 12-(phenyl-1-H-tetrazole-5-ylsulfonyl)-dodecyl ester (21.98 g, 45.9 mmol) in dry THF (200 ml) under nitrogen at 0° C. and then allowed to warm to room temperature. When TLC showed no starting material remaining the reaction mixture was quenched with a saturated aqueous solution of NH$_4$Cl at 0° C. followed by petrol/ethyl acetate (10:1, 50 ml). The organic phase was separated and the aqueous layer was extracted with petrol/ethyl acetate (10:1, 3×100 ml). The combined organic extracts were dried and evaporated. Column chromatography (petrol/ethyl acetate, 20:1) gave 2,2-dimethylpropanoic acid (22-bromo)-12-enyl-docos ester (12.60 g, 68%) as a colourless oil.

This oil was dissolved in IMS/THF (1:1, 70 ml), palladium on carbon (1 g, 10%) was added and the solution stirred under hydrogen for 1 hour. Filtration through Celite, concentration in vacuo and purification by column chromatography (petrol/ethyl acetate, 10:1) gave 22-bromodocosyl pivalate (11 g, 87%) as a white solid.

This white solid was mixed with 1-Phenyl-1H-tetrazole-5-thiol (4.40 g, 24.6 mmol) and anhydrous potassium carbotonate (6.81 g, 49.3 mmol) in acetone (250 ml) and stirred vigorously for 18 hours at room temperature. When TLC analysis indicated that the reaction was complete, water (50 ml) was added and the mixture was extracted with dichloromethane (1×200 ml, 2×100 ml). The combined organic phases were washed with brine (2×200 ml), dried and the solvent was evaporated to give a white solid, 2,2-Dimethylpropanoic acid 22-(1-phenyl-1H-tetrazole-5-ylsulfanyl) docosyl ester (13 g, 84%).

A solution of ammonium molybdate (VI) tetrahydrate (13.70 g, 11.09 mmol) in 35% H$_2$O$_2$ (50 ml) prepared and cooled in an ice bath was added to a stirred solution of the white solid (13 g, 22.18 mol) in THF/IMS (2:3) (150 ml) at 10° C. and stirred at room temperature for 2 hours. A further solution of ammonium molybdate (VI) tetrahydrate (6.85 g, 5.554 mmol) in 35% H$_2$O$_2$ (25 ml) was added and the mixture was stirred at room temperature for a further 18 hours. The mixture was poured into water (1 L) and extracted with dichloromethane (1×250 ml, 3×150 ml). The combined organic phases were washed with water (500 ml), dried and the solvent evaporated. Column chromatography (petrol/ethyl acetate, 5:1) gave compound A (2,2-dimethyl-propanoic acid 22-(1-phenyl-1H-tetrazole-5-ylsulfonyl)docosyl ester, 12.4 g, 90%) as a white solid δ$_H$: 7.61-7.60 (2H, m), 7.59-7.58 (3H, m), 4.04 (2H, t, J 6.65), 3.73 (2H, t, J 7.4), 1.95-1.92 (2H, m), 1.61 (2H, p, J 6.95), 1.50 (2H, p, J 6.65), 1.37-1.22 (34H, m), 1.19 (9H, s); δ$_c$: 178.60, 171.08, 153.47, 133.03, 131.40, 129.66, 125.04, 64.42, 60.34, 55.98, 38.68, 29.66, 29.60, 29.53, 29.47, 29.42, 29.18, 29.15, 28.85, 28.57, 28.10, 27.16, 25.87, 21.90, 20.99; ν$_{max}$/cm$^{-1}$: 2917, 2854, 1725, 1594, 1500, 1472, 1344, 1285, 1157

EXAMPLE 2

Compound B was prepared by the following method:

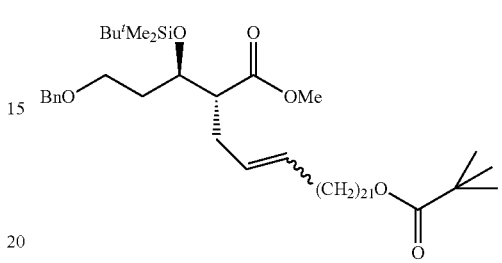

B (2R,3R)-5-benzyloxy-3-(tert-butyl-dimethyl-silanyloxy)-2-(oxo-ethyl)pentanoic acid methyl ester (3.7 g, 9.38 mmol) was prepared according to the method published in Koza, G.; Theunissen, C.; Al-Dulayymi, J. R.; Baird, M. S. Tetrahedron, 2009, 65, 10099. This was dissolved in dry THF (100 ml) along with compound A (6.39 g, 10.32 mmol) and stirred at −10° C. before the addition of lithium bis(trimethylsilyl)amide (14.6 ml, 15.48 mmol). The reaction mixture turned bright yellow and was left to reach r.t. and stirred for one hour. When TLC indicated the reaction was complete, it was quenched by the addition of saturated aqueous NH$_4$Cl (50 ml). The product was extracted with petrol/ethyl acetate (20:1, 3×150 ml), dried over MgSO$_4$, filtered and evaporated. Column chromatography (petrol/ethyl acetate, 20:1) gave (R)-2-[(E/Z)—(R)-1-(tert-butyl-dimethyl-silanyloxy)-3-benzyloxy-propyl]-26-(2,2-dimthyl-propionyloxy)-hexacos-3-enoic acid methyl ester (5 g, 67%) as a colourless oil [Found [M+Na]$^+$: 809.5982; C$_{48}$H$_{86}$O$_6$SiNa requires 809.6086; δ$_H$: 7.33-7.28 (2H, m), 7.25-7.22 (3H, m), 5.41-5.34 (1H, m), 5.28-5.19 (1H, m), 4.44 (2H, s), 4.02-3.99 (1H, m), 3.59 (3H, s), 3.55-3.48 (2H, m), 2.58-2.54 (1H, m), 2.25-2.20 (2H, m), 1.78 (2H, p, J 5.35), 1.57 (2H, p, J 6.6), 1.29-1.19 (49H, m), 1.15 (9H, s), 0.85-0.79 (6H, m); δ$_C$: 178.64, 174.00, 173.98, 138.48, 132.79, 128.31, 127.55, 127.46, 126.83, 72.89, 70.42, 66.24, 64.45, 52.24, 51.34, 51.24, 38.71, 33.74, 33.68, 32.53, 30.39, 29.70, 29.63, 29.60, 29.55, 29.51, 29.48, 29.36, 29.22, 29.10, 28.61, 27.27, 25.90, 17.95, −4.58, −4.87; ν$_{max}$/cm$^{-1}$: 2925, 2853, 1731, 1461, 1283, 1252, 1159, 1101.

EXAMPLE 3

Compound C was prepared by the following method:

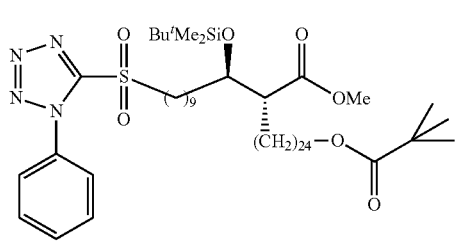

C

Palladium on carbon (1 g, 10%) was added to a solution of compound B (5 g, 6.35 mmol) in a mixture of THF (50 ml) and IMS (50 ml) and stirred under hydrogen for 2 days. Filtration through Celite and evaporation of the solvent was followed by column chromatography (petrol/ethyl acetate, 5:1) to give (R)-2-[(—(R)-1-(tert-butyl-dimethyl-silanyloxy)-3-hydroxy-propyl]-26-(2,2-dimthyl-propionyloxy)-hexacosanoic acid methyl ester (3 g, 67%) as a white solid.

This white solid in dichloromethane (20 ml) was added to a stirred suspension of PCC (2.40 g, 11.15 mmol) in dichloromethane (130 ml) at room temperature and the mixture stirred vigorously for 2 hrs. When TLC showed no starting material remained the mixture was poured petrol/ethyl acetate (10:1, 300 ml), filtered through a pad of silica and Celite, washed with petrol/ethyl acetate (10:1) and evaporated. Column chromatography (petrol/ethyl acetate, 10:1) gave (R)-2-[(R)-1-(tert-butyl-dimethyl-silanyloxy)-3-oxopropyl]-26-(2,2-dimethyl-propionyloxy)-hexacosanoic acid methyl ester (2.46 g, 82%) as a colourless oil.

Lithium bis(trimethylsilyl)amide (5.85 ml, 4.77 mmol) was added to a stirred solution of the colourless oil (2.46 g, 3.67 mmol) and 7-bromo (1-phenyl-1H-tetrazole-5-sulfonyl)heptyl (1.84 g, 4.77 mmol) in dry THF (100 ml) at −10° C. The reaction turned bright yellow and was left to reach r.t. and stirred for one hour under $N_2$. When TLC showed that the reaction was complete the reaction mixture was quenched with a saturated aqueous solution of $NH_4Cl$ (50 ml). The product was extracted with petrol/ethyl acetate (20:1, 3×150 ml), dried over $MgSO_4$, filtered and evaporated. Column chromotography (petrol/ethyl acetate, 20:1) gave (R)-2-[(E/Z)—(R)-10-bromo-1-(tert-butyl-dimethyl-silanyloxy)-dec-3-enyl]-26-(2,2-dimethyl-propionyloxy)-hexacosanoic acid methyl ester (2.3 g, 76%) as a colourless oil.

Palladium on carbon (0.3 g, 10%) was added to a stirred solution of this colourless oil (2.30 g, 2.68 mmol) in IMS/THF (1:1, 100 ml) and hydrogenated for 1 hour. The solution was filtered over a bed of Celite and the solvent was evaporated. Column chromatography (petrol/ethyl acetate, 10:1) gave (R)-2-[(R)-10-bromo-1-(tert-butyl-dimethyl-silanyloxy)-decyl]-26-(2,2-dimethylpropionyloxy)-hexacosanoic acid methyl ester (2.0 g, 81%) as a colourless oil.

1.8 g (2.093 mmol) of this oil was stirred with 1-phenyl-1H-tetrazole-5-thiol (0.41 g, 2.29 mmol), and anhydrous potassium carbotonate (0.63 g, 4.60 mmol) acetone/THF (30/15 ml) under reflux for 2 hours. When TLC indicated the reaction was complete it was quenched with water (50 ml) extracted with dichloromethane (1×100 ml, 2×75 ml). The combined organic layers were washed with brine (2×100 ml), dried and the solvent was evaporated. Column chromatography (petrol/ethyl acetate, 5:1) gave (R)-methyl 2-((R)-1-(tert-butyldimethylsilyloxy)-10-(1-phenyl-1H-tetrazol-5-ylsulfanyl)decyl)-26-(pivaloyloxy)hexacosanoate (1.70 g, 85%) as a colourless oil.

A solution of ammonium molybdate (VI) tetrahydrate (1.05 g, 0.85 mmol) in 35% $H_2O_2$ (15 ml), prepared and cooled in an ice bath was added to a stirred solution of this colourless oil (1.63 g, 1.70 mmol) in THF/IMS (15/20 ml) at 10° C. and stirred at room temperature for 2 hours. A further solution of ammonium molybdate (VI) tetrahydrate (0.52 g, 0.42 mmol) in 35% $H_2O_2$ (10 ml) was added and the mixture was stirred at room temperature for 18 hours. The mixture was poured into water (250 ml) and extracted with petrol/ethyl acetate (5:2, 2×200 ml). The combined organic layers were washed with water (100 ml), dried and the solvent was evaporated. Column chromatography (petrol/ethyl acetate, 5:1 and then 1:1) gave (R)-methyl 2-((R)-1-(tert-butyldimethylsilyloxy)-10-(1-phenyl-1H-tetrazol-5-ylsulfonyl)decyl)-26-(pivaloyloxy)hexacosanoate (compound C, 1.28 g, 76%) as a colourless oil. Found [M+Na]⁺: 1011.6958; $C_{55}H_{100}O_7SiN_4Na$ requires 1011.6974]; $[\alpha]^{20}_D$ −7.64 (c 0.89, $CHCl_3$); $\delta_H$: 7.71-7.69 (2H, m), 7.62-7.60 (3H, m), 4.04 (2H, t, J 6.6), 3.92-3.88 (1H, m), 3.73 (2H, t, J 7.85), 3.65 (3H, s), 2.54-2.50 (1H, m), 1.95 (2H, p, J 7.6), 1.61 (2H, p, J 6.9), 1.53-1.15 (67H, m, including a singlet at δ 1.19), 0.86 (9H, s), 0.04 (3H, s), 0.02 (3H, s); $\delta_C$: 178.66, 175.08, 153.48, 133.03, 131.43, 129.70, 125.04, 73.15, 64.46, 55.99, 51.58, 51.23, 38.71, 33.61, 29.55, 29.44, 29.39, 29.21, 28.87, 28.59, 28.13, 27.84, 27.43, 27.19, 25.89, 25.74, 23.73, 21.94, 17.96, −4.37, −4.93; $v_{max}$/cm⁻¹: 2925, 2853, 1731, 1463, 1344, 1284, 1254, 1154, 1099, 1074, 836, 775.

EXAMPLE 4

Compound D was prepared by the following method:

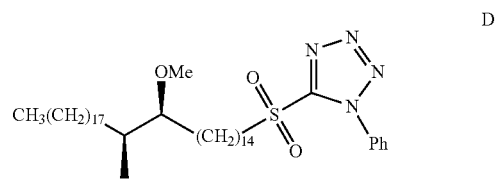

(8S,9S)-8-methoxy-9-methylheptacosanal and 2,2-dimethylpropionic acid-7-(1-phenyl-1H-tetrazol-5-ylsulfonyl)-heptyl ester were prepared using a method analogous to that described by Al Dulayymi, Baird, Roberts, Verschoor and Deysel in supplementary information to Tetrahedron 2007, 63, 2571-2592.

(8S,9S)-8-methoxy-9-methylheptacosanal (1.56 g, 3.56 mmol) and 2,2-dimethylpropionic acid-7-(1-phenyl-1H-tetrazol-5-ylsulfonyl)-heptyl ester (1.74 g, 4.27 mmol) were stirred in dry THF (50 ml) nitrogen at −10° C. Lithium bis(trimethylsilyl)amide (5.24 ml, 5.56 mmol, 1.06 M) was added dropwise between −12° C. and −5° C., the solution was stirred for 18 hrs. When TLC showed no starting material was left, dichloromethane (50 ml) and sat. aq. ammonium chloride (50 ml) were added. The aqueous layer was re-extracted with dichloromethane (2×100 ml) and the combined organic layers were dried and evaporated to give a crude product. This was purified via column chromatography eluting with petrol/ether (10:1) to give a colourless oil, (E/Z)-2,2-dimethyl-propionic acid 15-methoxy-16-methyl-tetratriacont-7-enyl ester (1.78 g, 81%). Palladium on charcoal (0.2 g, 10%) was added to a stirred solution of the above product (1.78 g, 2.87 mmol) in THF (5 ml) and IMS (40 ml). The mixture was stirred under hydrogen at atmospheric pressure. When no more hydrogen was being absorbed the catalyst was removed via suction filtration through a pad of celite and was washed with THF (50 ml). The filtrate was evaporated to give a colourless oil, (15S,16S)-15-methoxy-16-methyltetratriacontyl pivalate (1.57 g, 88%).

This colourless oil was added in THF (10 ml) was added slowly to a solution of lithium aluminium hydride (0.14 g, 3.79 mmol) in THF (20 ml) at −20° C. The reaction was allowed to reach RT then heated under reflux for 1 hr. When TLC showed no starting material was left the reaction was cooled to −20° C. and was quenched with sat. aq. sodium sulfate until a white precipitate formed. THF (30 ml) was added and the mixture was stirred for 30 mins, then filtered through a bed of silica and the solvent evaporated. The resulting solution was taken up in dichloromethane (50 ml) and washed with water (10 ml) and then dried. The solvent was evaporated and the crude product was purified via column chromatography eluting with petrol/ether (20:1, then 1:1) to give a white solid.

N-Bromosuccinimide (0.44 g, 2.46 mmol, 1.3 mol. equiv.) was added in portions over 15 mins to a stirred solution of the white solid (1.04 g, 1.89 mmol) and triphenylphosphine (0.56 g, 2.14 mmol, 1.13 equiv) in dichloromethane (20 ml) at 0° C. The mixture was stirred at RT for 1 hr, under TLC indicated completion of the reaction. It was quenched with sat. aq. sodium meta-bisulfite (25 ml) then the aqueous layer was re-extracted with dichloromethane (2×20 ml) and the combined organic extracts washed with water (50 ml), dried and evaporated. The residue was treated with petrol/ether (1:1, 50 ml) heated at reflux for 30 mins and then filtered and washed with petrol/ether (1:1, 25 ml). The filtrate was evaporated and the resultant residue purified via column chromatography eluting with petrol/ether (10:1) to give a white solid, (15S,16S)-1-bromo-15-methoxy-16-methyl-tetratriacontane (0.76 g, 83%).

This white solid (0.70 g, 1.14 mmol) in THF (3 ml) and acetone (3 ml) was added to a stirred solution of 1-phenyl-1H-tetrazole-5-thiol (0.22 g, 1.26 mmol, 1.1 mol. equiv.) and anhydrous potassium carbonate (0.55 g, 4.00 mmol, 3.5 mol. equiv.) in acetone (15 ml) at RT. The mixture was stirred at RT for 18 hrs, then the solvent was evaporated and the residue was diluted with petrol/ether (1:1, 20 ml) and water (20 ml). The aqueous layer was re-extracted with petrol/ether (1:1, 2×10 ml). The combined organic extracts were dried and evaporated to give a crude oil which was purified via column chromatography eluting with petrol/ether (10:1) to give a colourless oil, 5-((15S,16S)-15-methoxy-16-methyltetratriacontyl-1-sulfanyl)-1-phenyl-1H-tetrazole (0.76 g, 93%).

m-Chloroperbenzoic acid (0.52 g, 3.04 mmol, 3 mol. equiv.) in dichloromethane (5 ml) was added slowly to this colourless oil (0.72 g, 1.01 mmol) and sodium hydrogen carbonate (0.38 g, 4.56 mmol, 4.5 mol. equiv.) in dichloromethane (5 ml) at 5° C. The mixture was stirred for 18 hrs at RT, when TLC analysis indicated completion of the reaction. The solvent was evaporated and the resultant residue was diluted with ethyl acetate (5 ml) and slowly quenched with sat. aq. sodium metabisulfite (2 ml). The aqueous layer was re-extracted with ethyl acetate (2×10 ml) and the combined organic extracts were washed with sat. aq. sodium hydrogen carbonate (10 ml) and then water (20 ml). The organic extract was then dried and evaporated and the resultant yellow oil purified via column chromatography eluting with petrol/ether (1:1) to give a white solid, 5-((15S, 16S)-15-methoxy-16-methyltetratriacontyl-1-sulfonyl)-1-phenyl-1H-tetrazole (0.67 g, 89%), which showed $\delta_H$ (500 MHz, CDCl$_3$): 7.71-7.70 (2H, m), 7.69-7.61 (3H, m), 3.74 (2H, t, J 7.9 Hz), 3.34 (3H, s), 2.97-2.95 (1H, m), 1.96 (2H, pent, J 7.9 Hz), 1.63-1.58 (1H, m), 1.50 (2H, pent, J 7.6 Hz), 1.45-1.22 (56H, m), 0.89 (3H, t, J 6.6 Hz), 0.85 (3H, d, J 6.7 Hz); $\delta_C$ (125 MHz, CDCl$_3$): 153.5, 133.1, 131.5, 130.3, 125.1, 85.5, 57.7, 56.0, 35.3, 32.4, 31.9, 30.5, 30.0, 29.9, 29.7, 29.7, 29.62, 29.60, 29.5, 29.4, 29.2, 28.9, 26.5, 22.8, 22.0, 15.1, 14.4; $v_{max}$: 2947, 2852, 1321, 1164, 1097 cm$^{-1}$; $[\alpha]^{23}{}_D$=−6.28 (CHCl$_3$, 1.024 μmol); [Found M+Na$^+$: 753.50; C$_{43}$H$_{78}$N$_4$NaO$_3$S requires: 753.57].

EXAMPLE 5

Compound E was prepared as follows:

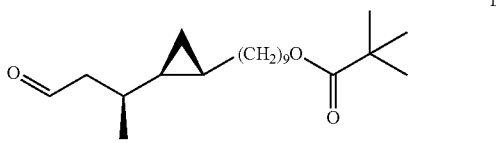

2,2-dimethyl-propionic acid 8-(1-phenyl-1H-tetrazole-5-sulfonyl)-octyl ester was prepared by a method analogous to that described by Al Dulayymi, Baird, Roberts, Verschoor and Deysel in supplementary information to Tetrahedron 2007, 63, 2571-2592.

Lithium hexamethyldisilazide (7.76 ml, 8.22 mmol, 1.06M) was added dropwise to a stirred solution of 2,2-dimethyl-propionic acid 8-(1-phenyl-1H-tetrazole-5-sulfonyl)-octyl ester (2.67 g, 6.32 mmol) and (1S,2R)-2-((S)-4-(tert-butyldiphenylsilyloxy)butan-2-yl)cyclopropanecarbaldehyde (1.93 g, 5.27 mmol) in dry THF (50 ml) under nitrogen at −20° C. The temperature rose to −10° C. during the addition of the base, and a yellow solution resulted. The mixture was allowed to reach RT and was stirred for 2 hrs, when TLC showed no starting material was left and then cooled to 0° C. and quenched with sat. aq. ammonium chloride (100 ml). The product was extracted with petrol/ether (1:1, 3×50 ml). The combined organic layers were washed with brine (100 ml), dried and evaporated to give an oil, which was purified via column chromatography eluting with petrol/ether (7:1) to give (E/Z)-9-((1R,2S)-2-((R)-1-(tert-butyldiphenylsilyloxy)propan-2-yl)cyclopropyl)non-8-enyl pivalate (2.28 g, 75%). Dipotassium azo-dicarboxylate (45.20 g, 232.70 mmol) was added to a stirred solution of this pivalate (4.47 g, 7.76 mmol) in THF (200 ml) and methanol (100 ml) at 10° C. under nitrogen, giving a yellow precipitate. A solution of glacial acetic acid (10 ml) and THF (20 ml) was added dropwise over 48 hrs, after which a white precipitate had formed. The mixture was cooled to 0° C. and poured slowly into sat. aq. sodium hydrogen carbonate (50 ml) and then extracted with petrol/ether (1:1, 3×100 ml). The combined organic layers were washed with water (50 ml), dried and evaporated to give a thick oil which slowly solidified. The residue was purified by column chromatography eluting in petrol/ether (10:1) to give a colourless oil, 2,2-dimethyl-propionic acid 9-((1S, 2R)-2-(S)-4-(tert-butyldiphenylsilyloxy)butan-2-yl)cyclopropyl)nonyl pivalate (4.14 g, 93%).

This colourless oil (4.14 g, 7.16 mmol) was dissolved in dry THF (20 ml) in a polyethylene vial under nitrogen at RT. Pyridine (2 ml) and HF.Pyridine (10.23 ml, 7.16 mmol) were added and the mixture stirred for 17 hrs at 45° C., when TLC showed no starting material was left. The mixture was diluted with petrol/ether (1:1, 20 ml) and neutralised with by adding to sat. aq. sodium hydrogen carbonate (25 ml) until no more carbon dioxide was liberated. The compound was extracted with petrol/ether (1:1, 2×50 ml) and washed with brine (100 ml), dried and evaporated. The resultant oil was purified via column chromatography eluting with petrol/ether (4:1) to give a colourless oil, 9-((1S,2R)-2-((S)-4-hydroxybutan-2-yl)cyclopropyl)nonyl pivalate (1.92 g, 79%).

This colourless oil (0.42 g, 1.23 mmol) was added to a stirred suspension of PCC (0.67 g, 3.09 mmol, 2.5 mol.

equiv.) in dichloromethane (10 ml). The reaction mixture was stirred for 2 hrs at RT, when TLC analysis confirmed completion of the reaction, and diluted with ether (50 ml). The mixture was filtered through a bed of silica and washed with ether (2×10 ml), the solvent evaporated and the product was purified via column chromatography eluting with petrol/ether (5:2) to give a colourless oil, 9-((1S,2R)-2-((S)-4-oxobutan-2-yl)cyclopropyl)nonyl pivalate (0.39 g, 93%), which showed $\delta_H$ (500 MHz, CDCl$_3$): 9.78 (1H, s), 2.50 (1H, ddd, J 15.75, 6.3, 1.9 Hz), 2.35 (1H, ddd, J 15.75, 7.9, 2.5 Hz), 1.61 (2H, pent, J 6.6 Hz), 1.32-1.13 (26H, m), 1.00 (3H, d, J 6.65 Hz), 0.49 (1H, m), 0.34-0.21 (3H, m); $\delta_C$ (125 MHz, CDCl$_3$): 202.9, 178.6, 64.4, 51.4, 38.7, 34.1, 33.9, 29.6, 29.51, 29.48, 29.2, 28.6, 27.2, 25.9, 25.6, 20.0, 18.8, 11.4; $v_{max}$: 2924, 2878, 1727 cm$^{-1}$; $[\alpha]^{22}{}_D$=+20.47 (CHCl$_3$, 1.076 μmol); [Found M+Na$^+$: 361.24; C$_{21}$H$_{38}$NaO$_3$ requires: 361.27].

EXAMPLE 6

Compound F was prepared as follows:

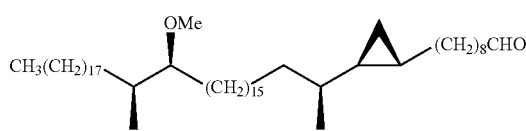

Lithium hexamethyldisilazide (0.923 ml, 0.978 mmol, 1.06M) was added dropwise to a stirred solution of compound D (670 mg, 0.903 mmol) and compound E (255 mg, 0.752 mmol) in dry THF (10 ml) under nitrogen at −20° C. The reaction mixture rose to −10° C. during the addition of the base, and a yellow solution resulted. The mixture was allowed to reach RT and was stirred for 1 hr, when TLC showed no starting material was left. The reaction mixture was cooled to 0° C. and quenched with sat. aq. ammonium chloride (10 ml). The product was extracted with petrol/ether (1:1, 3×10 ml). The combined organic layers were washed with brine (20 ml), dried and evaporated to give an oil, which was purified via column chromatography eluting with petrol/ether (20:1) to give 9-((1S,2R)-2-[(E/Z)-(2S,19S,20S)-19-methoxy-20-methyloctatriacont-4-en-2-yl]cyclopropyl)nonyl pivalate (410 mg, 54%). Dipotassium azodicarboxylate (2.49 g, 12.83 mmol, 30 mol. equiv.) was added to a stirred solution of this compound (410 mg, 0.487 mmol) in THF (20 ml) and methanol (10 ml) at 10° C. under nitrogen, giving a yellow precipitate. A solution of glacial acetic acid (1 ml) and THF (2 ml) was added dropwise over 48 hrs, after which a white precipitate had formed. The mixture was cooled to 0° C. and poured slowly into sat. aq. sodium hydrogen carbonate (5 ml) and then extracted with petrol/ether (1:1, 3×25 ml). The combined organic layers were washed with water (10 ml), dried and evaporated to give a thick oil which slowly solidified. The residue was purified via column chromatography eluting in petrol/ether (10:1) to give a colourless oil, 9-((1S,2R)-2-((2S,19S,20S)-19-methoxy-20-methyloctatriacontan-2-yl)cyclopropyl) nonyl pivalate (400 mg, 97%).

A solution of this colourless oil (400 mg, 0.4737 mmol) in THF (5 ml) was added slowly Lithium aluminium hydride (36.0 mg, 0.9479 mmol, 2 mol. equiv.) in THF (5 ml, HPLC grade) at −20° C. under nitrogen. The reaction was allowed to reach RT, then heated under reflux for 1 hr. When TLC showed no starting material was left the reaction mixture was cooled to −20° C. and was quenched with sat. aq. sodium sulfate until a white precipitate formed. The resultant mixture was stirred for 30 mins and then filtered through a bed of silica and the solvent evaporated. The product was purified via column chromatography eluting with petrol/ether (1:1) to give a colourless oil, 9-((1S,2R)-2-((2S,19S,20S)-19-methoxy-20-methyloctatriacontan-2-yl)cyclopropyl)nonan-1-ol (260 mg, 72%).

This colourless oil (0.26 g, 0.343 mmol) was added to a stirred suspension of PCC (0.22 g, 1.03 mmol, 3 mol. equiv.) in dichloromethane (10 ml). The reaction mixture was stirred for 1 hr at RT, when TLC analysis confirmed completion of the reaction, then diluted with ether (10 ml). The mixture was filtered through a bed of silica and washed with ether (2×5 ml), the solvent evaporated and the product was purified via column chromatography eluting with petrol/ether (10:1) to give a colourless oil, 9-((1R,2R)-2-((2S,19S,20S)-19-methoxy-20-methyloctatriacontan-2-yl)cyclopropyl)-nonanal (0.24 g, 96%), which showed $\delta_H$ (500 MHz, CDCl$_3$): 9.77 (1H, br. t, J 1.85 Hz), 3.38 (3H, s), 2.97-2.95 (1H, m), 2.43 (2H, dt, J 1.85, 7.55 Hz), 1.99-1.97 (1H, m), 1.65-1.61 (1H, m), 1.56 (2H, m), 1.40-1.09 (78H, br. m including br. s at 1.27), 0.89 (6H, dt, J 2.85, 6.6 Hz), 0.85 (3H, d, J 6.6 Hz), 0.48-0.43 (1H, m), 0.22-0.18 (1H, m), 0.17-0.14 (1H, m), 0.13-0.09 (1H, m); $\delta_C$ (125 MHz, CDCl$_3$): 205.1, 85.5, 65.6, 57.7, 43.9, 38.1, 37.4, 35.4, 34.4, 32.8, 32.4, 31.9, 30.5, 30.0, 29.9, 29.7, 29.6, 29.5, 29.4, 29.3, 27.6, 27.3, 26.2, 25.8, 22.7, 19.7, 18.6, 16.5, 14.3, 10.5; $v_{max}$: 2984, 2875, 1724 cm$^{-1}$; $[\alpha]^{19}{}_D$=−3.45 (CHCl$_3$, 1.247 μmol); [Found M+Na$^+$: 781.72; C$_{52}$H$_{102}$NaO$_2$ requires: 781.78].

EXAMPLE 7

Compound G was prepared as follows:

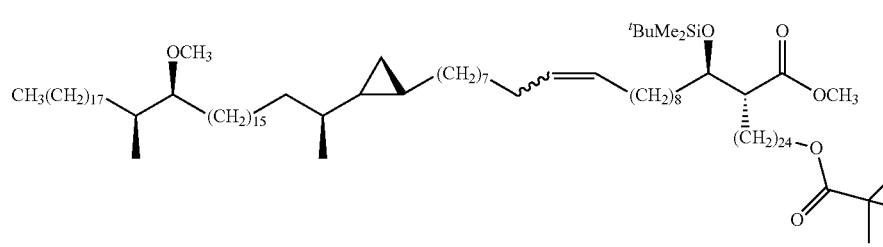

Lithium bis(trimethylsilyl)amide (0.96 ml, 1.02 mmol, 1.06 M) was added to a stirred solution of compound F (0.494 g, 0.651 mmol) and compound C (0.773 g, 0.781 mmol) in dry THF (15 ml) at 0-5° C. The solution turned bright yellow/orange and was left to reach room temperature and stirred for 1 hour under $N_2$ (g). When TLC showed no starting material remaining the reaction was quenched by addition of a saturated aqueous solution of $NH_4Cl$ (10 ml) at −20° C. The mixture was extracted with petrol/ethyl acetate (1:1, 3×15 ml) and the combined organic layers were dried, filtered and evaporated. Column chromatography (petrol/ethyl acetate, 20:1) gave (2R)-methyl 2-((1R)-1-(tert-butyldimethylsilyloxy)-19-((1R)-2-((2S,19S,20S)-19-methoxy-20-methyloctatriacontan-2-yl)cyclopropyl)nonadec-10-enyl)-26-(pivaloyloxy)hexacosanoate (0.849 g, 0.558 mmol, 86%) as a colourless oil; $[\alpha]_D^{23}$ −8.54 (c 1.19, $CHCl_3$). This showed $v_{max}$(film)/cm$^{-1}$: 2923 (C—H), 2853 (C—H), 1732 (C=O) and 1463; $\delta_H$: 0.02 (3H, s, $SiCH_3$), 0.05 (3H, s, $SiCH_3$), 0.09-0.22 (3H, m, 3×cyclopropane CH), 0.41-0.48 (1H, m, cyclopropane CH), 0.68 (1H, m, CH), 0.83-0.90 (23H, m, including a singlet at 0.87, SiC$(CH_3)_3$), 1.26 (151H, m, including a singlet at 1.20), 1.62 (5H, m), 1.96 (2H, m, $CH_2$), 2.02 (1H, m, CH), 2.53 (1H, ddd, J 3.6, 7.2 and 11.0, $CHCH(CH_2)CO$), 2.96 (1H, m, $CH_2CH(OCH_3)CH_2$), 3.35 (3H, s, $OCH_3$), 3.66 (3H, s, $OCH_3$), 3.91 (1H, m, $CH_2CH(O)CH$), 4.05 (2H, t, J 6.6, $CH_2CH_2O$) and 5.37 (2H, m, $CH_2CH=CHCH_2$); $\delta_C$: −4.9, −4.4, 10.5, 14.1, 14.9, 18.0, 18.6, 19.7, 22.6, 22.7, 23.7, 25.8, 25.9, 26.1, 26.2, 27.2, 27.3, 27.5, 27.6, 27.8, 28.6, 29.1, 29.2, 29.2, 29.3, 29.4, 29.5, 29.5, 29.6, 29.6, 29.7, 29.7, 29.8, 30.0, 30.0, 30.1, 30.5, 31.9, 32.4, 32.6, 33.7, 34.5, 35.3, 37.4, 38.1, 51.2, 51.6, 57.7, 64.5, 73.2, 85.5, 129.8, 129.9, 130.3, 130.4, 143.2, 175.2 and 178.7.

EXAMPLE 8

Compound H, a sulfur-containing mycolic acid derived antigen of the present invention was prepared as follows:

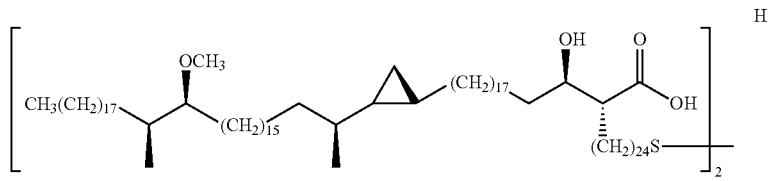

Dipotassium azodicarboxylate was added in excess to a stirred solution of compound G (0.840 g, 0.552 mmol) in dry THF (10 ml) and methanol (5 ml) at 0° C. under $N_2$ (g). Acetic acid (2 ml) in dry THF (4 ml) was added dropwise in small portions throughout the day at 0° C. The following morning further dipotassiumazodicarboxylate followed by more of the acetic acid in THF was added. Again, after stirring overnight, more dipotassiumazodicarboxylate was added, followed by more of the acetic acid in THF. After stirring for a 3$^{rd}$ night the reaction was quenched by adding the reaction mixture in small portions to a saturated solution of aqueous $NaHCO_3$ (15 ml). The mixture was extracted with petrol/ethyl acetate (5:2, 3×25 ml) and the combined organic layers were dried, filtered and evaporated. Column chromatography (petrol, ethyl acetate, 20:1) gave (2R)-methyl 2-((1R)-1-(tert-butyldimethylsilyloxy)-19-((1R)-2-((2S,19S, 20S)-19-methoxy-20-methyloctatriacontan-2-yl)cyclopropyl)nonadecyl)-26-(pivaloyloxy)hexacosanoate (0.727 g, 0.477 mmol, 86%) as a colourless oil.

This colourless oil (0.71 g, 0.47 mmol) was added to a stirred solution of potassium hydroxide (0.39 g, 6.99 mmol) in a mixture of THF (10 ml), methanol (10 ml) and water (1 ml). The mixture was heated under reflux at 70° C. and monitored by TLC. After ~3 hours, when TLC showed no starting material remaining the reaction was quenched with water (10 ml) and extracted with ethyl acetate (3×15 ml). The combined organic extracts were dried, filtered and evaporated. Column chromatography (petrol/ethyl acetate, 10:1) gave (2R)-methyl 2-((1R)-1-(tert-butyldimethylsilyloxy)-19-((1R)-2-((2S,19S,20S)-19-methoxy-20-methyloctatriacontan-2-yl)cyclopropyl)nonadecyl)-26-hydroxyhexacosanoate (0.583 g, 0.41 mmol, 86%) as a white solid.

A solution of this white solid (0.474 g, 0.327 mmol) and triethylamine (2 ml) in dry dichloromethane (25 ml) was cooled to −20° C. under $N_2$ (g) and stirred for 30 minutes, followed by the addition of toluene sulfonyl chloride (0.081 g, 0.425 mmol) in one portion. The solution was kept in the refrigerator overnight. When TLC showed no starting material remaining the solvent was evaporated. Column chromatography (petrol/ethyl acetate, 10:1) gave (2R)-methyl 2-((1R)-1-(tert-butyldimethylsilyl)oxy)-19-((1R)-2-((2S, 19S,20S)-19-methoxy-20-methyloctatriacontan-2-yl)cyclopropyl)nonadecyl)-26-(tosyloxy) hexacosanoate (0.333 g, 0.211 mmol, 65%) as a colourless oil.

A solution of this colourless oil (0.399 g, 0.251 mmol) and potassium thioacetate (0.115 g, 1.003 mmol) in acetone (15 ml) was stirred at room temperature overnight. When TLC showed that no starting material remained the solvent was evaporated. Column chromatography (petrol/ethyl acetate, 20:1) gave (2R)-methyl 26-(acetylthio)-2-((1R)-1-(tert-butyldimethylsilyloxy)-19-((1R)-2-((2S,19S,20S)-19-methoxy-20-methyloctatriacontan-2-yl)cyclopropyl)nonadecyl)hexanoate (0.227 g, 0.152 mmol, 61%) as a colourless oil.

The colourless oil (50 mg, 0.0333 mmol) was dissolved in dry THF (4 ml) in a dry polyethylene vial under $N_2$ (g) at 0° C. Pyridine (98.2 mg, 7.77 mmol, 0.1 ml) and HF.Pyridine (88 mg, 0.8 ml) were added and the mixture stirred at 45° C. overnight. When TLC showed no starting material remaining, the mixture was added slowly to a saturated aqueous solution of $NaHCO_3$ (10 ml). The solution was extracted with petrol/ethyl acetate (1:1, 3×15 ml) and the combined organic extracts were dried, filtered and evaporated. Column chromatography (petrol/ethyl acetate, 10:1) gave (2R)-methyl 26-(acetylthio)-2-((1R)-1-hydroxy-19-((1R)-2-((2S, 19S,20S)-19-methoxy-20-methyloctatriacontan-2-yl)cyclopropyl)nonadecyl)hexacosanoate (41.1 mg, 0.0299 mmol, 90%) as a white solid.

This white solid (14 mg, 0.010 mmol) was suspended in a 5% aqueous solution of TBAH (2 ml) and the solution was heated to 100° C. overnight. After this time TLC showed that the reaction was complete. The solution was cooled to room temperature and acidified to pH 1 with 1 M HCl and then extracted with diethyl ether (3×15 ml). The combined organic layers were dried, filtered and the solvent evaporated. Column chromatography (chloroform/methanol, 10:1) gave (2R)-2-((1R)-1-hydroxy-19-((1R)-2-((2S,19S, 20S)-19-methoxy-20-methyloctatriacontan-2-yl)cyclopropyl)nonadecyl)-26-mercaptohexacosanoic acid (7.7 mg, 0.0058 mmol, 58%) as a white solid; $[\alpha]_D^{2z}$ −2.78 (c 0.77, CHCl$_3$). This showed $\delta_H$: 0.08-0.20 (3H, m, 3×cyclopropane CH), 0.44 (1H, m, cyclopropane CH), 0.66 (1H, m, CH), 0.86 (3H, d, J 6.9, CH$_3$CH), 0.89 (3H, t, J 7.0, CH$_3$CH$_2$), 0.90 (3H, d, J 6.6, CH$_3$CH), 1.26 (144H, m), 1.67 (8H, m), 2.47 (1H, dt, J 5.4 and 9.1 CHCH(CH$_2$)CO), 2.69 (2H, t, J 7.4, CH2CH2S), 2.97 (1H, m, CH$_2$CH(OCH$_3$)CH$_2$), 3.35 (3H, s, OCH$_3$) and 3.91 (1H, m, CH2CH(OH)CH$_2$).

EXAMPLE 9

The following sulfur-containing linker compound I was prepared using the steps described below:

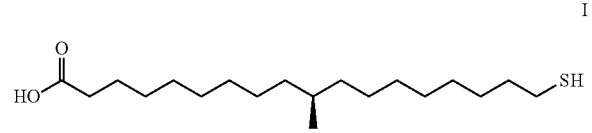 [SMILES: C[C@H](CCCCCCCCS)CCCCCCCCC(=O)O]

I

Magnesium turnings (13.50 g, 0.56 mol) were stirred in dry THF (100 ml) under N$_2$ (g). 2-(6-Bromohexyloxy) tetrahydro-2H-pyran (60.95 g, 0.23 mol) in dry THF (100 ml) was added slowly whilst heating gently with a heat gun. After all the solution was added the reaction mixture was heated under reflux for 30 min.

A stirred solution of S citronellyl bromide (10.00 g, 45.6 mmol) in dry THF (100 ml) was cooled to −78° C. under N$_2$ (g). The THF solution of (6-(tetrahydro-2H-pyran-2-yloxy) hexyl)magnesium bromide was transferred into the same vessel and the resultant mixture was cooled to −78° C. LiCuCl$_4$ (0.1 M in THF, 8 ml, 0.8 mmol) was added slowly in one portion and the temperature was seen to rise. The solution was left in the cooling bath for 2 days during which it slowly warmed to ambient temperature. The reaction was quenched with a saturated aqueous solution of NH$_4$Cl (100 ml) and the resultant bright blue solution was extracted with ether (3×100 ml). The combined organic phases were washed with brine (100 ml), dried, filtered and evaporated. Flash distillation gave 2-((R)-9,13-dimethyltetradec-12-enyloxy)tetrahydro-2H-pyran (10.28 g, 31.7 mmol, 70%) as a colourless oil.

Following a known procedure, a stirred solution of this colourless oil (8.00 g, 24.7 mmol) in dichloromethane (200 ml) was cooled to −78° C. prior to treatment with O$_3$ until a blue colour (liquid O$_3$) was seen to persist in the cooled solution. N$_2$ (g) was subsequently bubbled through the solution to remove excess O$_3$ and avoid danger on warming. Triphenylphosphine (6.47 g, 24.7 mmol) was added to the cold solution, which was warmed to ambient temperature and stirred overnight. The solvent was removed by rotary evaporation. Column chromatography (petrol/ether, 2:1) gave (4R)-4-methyl-12-(tetrahydro-2H-pyran-2-yloxy)dodecanal (5.81 g, 19.5 mmol, 80%) as a colourless oil.

(5-Carboxypentyl)triphenylphosphonium bromide (18.3 g, 40.2 mmol) was dissolved in 3:1 dry toluene/dry DMSO (200 ml). The solution was cooled to 0° C. and lithium bis(trimethylsilyl)amide (1.06 M in THF, 79.4 ml, 84.2 mmol) was slowly added maintaining a temperature of less than 0.3° C. The resultant bright red orange solution was warmed to ambient temperature over 3 hours and stirred at ambient temperature for a further 1 hour. The solution was cooled to −15° C. and (4R)-4-methyl-12-(tetrahydro-2H-pyran-2-yloxy)dodecanal (5.7 g, 19.1 mmol) was added as a solution in dry toluene (15 ml); the temperature was seen to rise on this addition. The solution was allowed to slowly return to ambient temperature and stirred overnight. A saturated aqueous solution of NH$_4$Cl (200 ml) was added and the mixture extracted with ethyl acetate (4×100 ml). The combined organic phases were washed with brine (100 ml), dried, filtered and evaporated. Column chromatography (petrol/ethyl acetate, 5:2) gave (10R)-10-methyl-18-(tetrahydro-2H-pyran-2-yloxy)octadec-6-enoic acid (3.85 g, 9.72 mmol, 51%) as a colourless oil.

Palladium on carbon (10%, 2.0 g) was slowly added under a stream of N$_2$ (g) to a stirred solution of this colourless oil (3.84 g, 9.69 mmol) in methanol (50 ml). The flask was connected to a hydrogenation apparatus which was purged of any air by repeated application of vacuum followed by refilling the system with H$_2$ (g). The reaction was monitored by observing the amount of H$_2$ (g) absorbed by a burette that is part of the apparatus. When the burette reading was steady the reaction was complete. The reaction mixture was then filtered through a pad of Celite®, which was washed with copious methanol. The solvent was removed by rotary evaporation. The residue was suspended in dichloromethane (50 ml), washed with brine (20 ml), dried, filtered and evaporated. Column chromatography (petrol/ether, 1:1) gave (10S)-10-methyl-18-(tetrahydro-2H-pyran-2-yloxy) octadecanoic acid (3.14 g, 7.88 mmol, 81%) as a colourless oil.

p-Toluene sulfonic acid monohydrate (372 mg, 1.95 mmol) was added to a stirred solution of this colourless oil (3.05 g, 7.82 mmol) in THF (25 ml), methanol (100 ml) and water (5 ml) at room temperature. The mixture was heated under reflux for 30 min. When TLC showed no starting material remaining a saturated aqueous solution of NaHCO$_3$ (100 ml) and petrol/ethyl acetate (1:1, 100 ml) were added. The layers were separated and the aqueous layer was extracted with petrol/ethyl acetate (1:1, 3×100 ml). The combined organic phases were washed with brine (100 ml), dried, filtered and evaporated. Column chromatography (petrol/ether, 2:1) gave (S)-methyl 18-hydroxy-10-methyl-octadecanoate (1.87 g, 5.70 mmol, 74%) as a colourless oil.

N-Bromosuccinimide (1.22 g, 6.86 mmol) was added in portions to a stirred solution of this colourless oil (1.50 g, 4.57 mmol) and triphenylphosphine (1.80 g, 6.86 mmol) in dichloromethane (50 ml) at 0° C. The reaction was stirred at room temperature for 1 hour or until there was no starting material remaining. The reaction was quenched with a saturated aqueous solution of Na$_2$S$_2$O$_5$ (50 ml). The reaction mixture was separated and the aqueous layer extracted with dichloromethane (2×50 ml). The combined organic layers were washed with water, dried, filtered and evaporated to give a residue. This was treated with a mixture of petrol/ ethyl acetate (1:1) (50 ml) and heated under reflux for 30 min. The solution was filtered, washed with petrol/ethyl acetate (1:1) and the solvent evaporated. Column chromatography (petrol/ethyl acetate, 5:1) gave (S)-methyl 18-bromo-10-methyloctadecanoate (1.56 g, 3.98 mmol, 87%) as a colourless oil.

A solution of this colourless oil (500 mg, 1.28 mmol) and thiourea (148 mg, 1.94 mmol) in ethanol (10 ml) was heated under reflux for 2.5 hours. The solvent was evaporated and 5 M NaOH (4 ml) was added slowly with stirring and the solution was heated under reflux for another 2 hours. The aqueous solution was cooled in an ice bath and acidified with dilute HCl. The solution was then extracted with ether (3×15 ml), dried, filtered and evaporated. Column chromatography (petrol/ether, 1:1) gave (S)-18-mercapto-10-methyloctadecanoic acid (217 mg, 0.66 mmol, 51%) as a colourless oil;

{Found (M+Na)$^+$: 353.2471, C$_{19}$H$_{38}$O$_2$SNa requires: 353.2485}. This showed $v_{max}$(film)/cm$^{-1}$: 3027 (broad OH), 2924 (C—H saturated), 2853 (C—H saturated), 2674 (S—H), 1708 (C=O) and 1463; $\delta_H$: 0.85 (3H, d, J 6.3, CH$_3$CH), 1.08 (2H, m, CH$_2$), 1.29 (23H, m, 11×CH$_2$ and CH), 1.63 (4H, m, 2×CH$_2$), 2.36 (2H, t, J 7.4, CH$_2$CH$_2$CO) and 2.54 (2H, q, J 7.4, CH$_2$CH$_2$SH); $\delta_C$: 19.7, 24.6, 24.7, 27.0, 28.4, 29.0, 29.1, 29.3, 29.5, 29.6, 29.9, 32.7, 34.0, 34.1, 37.1 and 180.3.

EXAMPLE 10

An sulfur-containing linker compound J was prepared as follows:

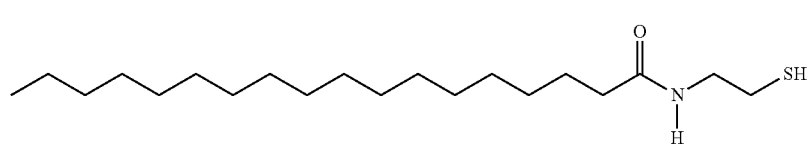

Stearic acid (8.53 g, 30.0 mmol) was added to a solution of N-hydroxy succinimide (3.45 g, 30.0 mmol) in dry ethyl acetate (130 ml). A solution of DCC (6.18 g, 30 mmol) in dry ethyl acetate (10 ml) was added and the reaction mixture was stirred overnight at room temperature. DCU was removed by filtration and the filtrate was concentrated under reduced pressure. Recrystallisation (ethanol) gave 2,5-dioxopyrrolidin-1-yl stearate (8.51 g, 22.3 mmol, 74%) as a white solid.

This white solid (5.29 g, 13.9 mmol) and 2-mercaptoethylamine hydrochloride (2.36 g, 20.8 mmol) were dissolved in dry dichloromethane (140 ml). Triethylamine (4.20 g, 5.8 ml, 41.6 mmol) that was dissolved in dry dichloromethane (5 ml) was added to the solution resulting in precipitation of a white solid. The reaction was allowed to stir overnight at room temperature. The following morning ethyl acetate (20 ml) and ethanol (10 ml) were added to form a clear solution. The organic solution was washed with dilute acid (3×15 ml) and water (2×15 ml) and the combined organic layers were dried, filtered and evaporated. Recrystallisation (chloroform) gave N-(2-mercaptoethyl)stearamide (2.66 g, 7.76 mmol, 56%) as a white solid; m.p: 63-65° C.; {Found (M+Na)$^+$: 366.2818, C$_{20}$H$_{41}$NOSNa requires: 366.2806}. This showed $v_{max}$(nujol)/cm$^{-1}$: 3300 (N—H), 2920 (C—H saturated), 2853 (C—H saturated), 1640 (C=O), 1550 and 1464; $\delta_H$: 0.89 (3H, t, J 6.9, CH$_3$CH$_2$), 1.26 (28H, m), 1.64 (2H, m), 2.20 (2H, t, J 7.6, CH$_2$CH$_2$CO), 2.68 (2H, dt, J 6.4 and 8.4, NHCH$_2$CH$_2$SH), 3.45 (2H, q, J 6.2, NHCH$_2$CH$_2$SH) and 5.8 (1H, br s, NH); $\delta_C$: 14.1, 22.7, 24.8, 25.7, 29.3, 29.4, 29.5, 29.6, 29.7, 29.7, 31.9, 36.8, 42.2 and 173.3.

EXAMPLE 11

Compound K was prepared as follows:

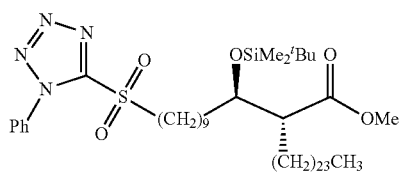

Lithium bis(trimethylsilyl)amide (4.14 ml, 4.39 mmol, 1.06 M) was added dropwise to a stirred solution of (R)-2-[(R)-1-(tert-butyldimethylsilanyloxy)-3-oxo-propyl]-hexacosanoic acid methyl ester (130) (1.30 g, 2.25 mmol) and 7-(1-phenyl-1H-tetrazol-5-ylsulfonyl)heptyl pivalate (160) (1.20 g, 2.93 mmol, 1.2 mol. equiv.) in dry THF (50 ml) at −15° C. The mixture was then stirred for 18 hrs at RT, when TLC analysis indicated completion of the reaction. Sat. aq. ammonium chloride (20 ml) and petrol/ether (1:1, 50 ml) were added. The aqueous layer was re-extracted with petrol/ether (1:1, 3×50 ml) and the combined organic extracts washed with brine (50 ml), dried and evaporated to give a yellow oil. The crude product was purified by column chromatography eluting with petrol/ether (20:1) to give a colourless oil, methyl 2-((R-(E,Z)-1-(tert-butyldimethylsilyloxy)-10-(pivaloyloxy)dec-3-nyl)hexacosanoate (1.23 g, 72%). Palladium on charcoal (10%, 0.5 g) was added to a stirred solution of methyl 2-((R-(E,Z)-1-(tert-butyldimethylsilyloxy)-10-(pivaloyloxy)dec-3-enyl)hexacosanoate (1.23 g, 1.54 mmol) in ethanol (20 ml) and THF (20 ml). The mixture was stirred while being hydrogenated at atmospheric pressure, and when hydrogen absorption was complete was filtered through a pad of celite and washed with ethyl acetate (100 ml). The filtrate was evaporated to give a colourless oil, methyl 2-((1R,2R)-1-(tert-butyldimethylsilyloxy)-10-(pivaloyloxy)decyl)hexacosanoate (1.12, 93%).

This colourless oil (1.10 g, 1.14 mmol) in THF (10 ml) was added to a stirred solution of potassium hydroxide (1.19 g, 21.18 mmol, 15 mol. equiv.) in THF (20 ml), methanol (20 ml) and water (2 ml). The mixture was heated to 70° C. and reflux was maintained for 2 hrs. When TLC analysis indicated completion of the reaction the mixture was quenched with water (10 ml) and the aqueous layer extracted with ethyl acetate (3×50 ml). The combined organic extracts were dried and evaporated and the crude product purified via column chromatography eluting with petrol/ether (5:2) to give a colourless oil, methyl 2-((1R,2R)-1-(tert-butyldimethylsilyloxy)-10-hydroxydecyl)hexacosanoate (0.66 g, 67%).

Triphenyl phosphine (0.29 g, 1.12 mmol, 1.2 mol. equiv.) was added to a stirred solution of the colourless oil (0.65 g, 0.935 mmol) in dry dichloromethane (20 ml) and then sodium hydrogen carbonate (0.10 g) was added. The mixture was cooled to 0° C. and N-bromosuccinimide (0.22 g, 1.22 mmol, 1.3 mol. equiv.) was added portion wise over 10 mins at 0-4° C. The reaction was stirred for 1 hr at 0-3° C., when TLC analysis showed completion of the reaction, sat. aq. sodium bisulfate (10 ml). The aqueous layer was re-extracted with dichloromethane (2×20 ml) and the combined organic layers were washed with water (20 ml), dried and the solvent evaporated. The resultant crude product was taken up in petrol/ether (1:1, 40 ml) and the mixture stirred for 30 mins, then the triphenylphosphonium oxide was filtered was washed with petrol/ether (1:1, 20 ml). The solvent was evaporated and the crude product purified via column chromatography eluting with petrol/ether (20:1) to give a white solid, methyl 2-((1R,2R)-10-bromo-1-(tert-butyldimethylsilyloxy)decyl)hexacosanoate (0.54 g, 76%).

The white solid (0.54 g, 0.71 mmol) was dissolved in THF (1.5 ml) and acetone (1.5 ml) and added to a stirred solution of 1-phenyl-1H-tetrazole-5-thiol (0.15 g, 0.857 mmol, 1.2 mol. equiv.) and anhydrous potassium carbonate (0.29 g, 2.14 mmol, 3 mol. equiv.) in acetone (10 ml, HPLC grade) at RT. The mixture was stirred at RT for 18 hrs, then the solvent was evaporated and the residue was diluted with petrol/ether (1:1, 20 ml) and water (20 ml). The aqueous layer was re-extracted with petrol/ether (1:1, 3×10 ml). The combined organic extracts were dried and evaporated to give a crude oil which was purified via column chromatography eluting with petrol/ether (10:1) to give a colourless oil, methyl 2-((1R,2R)-1-(tert-butyldimethylsilyloxy)-10-(1-phenyl-1H-tetrazol-5-ylthio)decyl)hexacosanoate (0.45 g, 73%).

m-Chloroperbenzoic acid (0.39 g, 1.58 mmol, 3 mol. equiv) in dichloromethane (2 ml) was added slowly to a stirred solution of the colourless oil (0.45 g, 0.53 mmol) and sodium hydrogen carbonate (0.20 g, 2.37 mmol, 4.5 mol. equiv.) in dichloromethane (5 ml) at 5° C. The mixture was stirred for 18 hrs at RT, when TLC analysis indicated completion of the reaction, and the solvent was evaporated. The resultant residue was diluted with ethyl acetate (5 ml) and slowly quenched with sat. aq. sodium metabisulfite (2 ml). The aqueous layer was re-extracted with ethyl acetate (2×10 ml) and the combined organic extracts were washed with sat. aq. sodium hydrogen carbonate (10 ml) and then water (20 ml). The organic extract was then dried and evaporated and the resultant yellow oil purified via column chromatography eluting with petrol/ether (1:1) to give a white solid, methyl 2-((1R,2R)-1-(tert-butyldimethylsilyloxy)-10-(1-phenyl-1H-tetrazol-5-ylsulfonyl)decyl)hexacosanoate (0.35 g, 75%), which showed $\delta_H$ (500 MHz, CDCl$_3$): 7.71-7.70 (2H, m), 7.64-7.60 (3H, m), 3.92-3.89 (1H, m), 3.74 (2H, t, J 8.2 Hz), 3.66 (3H, s), 2.53 (1H, ddd, J 3.8, 6.95, 11.05 Hz), 1.96 (2H, dist. pent, J 7.9 Hz), 1.51-1.20 (60H, br. m including br. s at 1.26), 0.89 (3H, t J 6.6 Hz), 0.87 (9H, s), 0.05 (3H, s), 0.02 (3H, s); $\delta_C$ (125 MHz, CDCl$_3$): 175.1, 154.5, 133.8, 130.0, 129.8, 123.9, 73.2, 61.8, 51.6, 51.2, 33.7, 33.4, 31.9, 29.8, 29.7, 29.6, 29.6, 29.4, 29.4, 29.1, 29.0, 28.7, 27.9, 27.7, 27.1, 25.8, 23.8, 22.7, 18.0, 15.2, 14.1, −4.4, −4.9; $v_{max}$: 2919, 2848, 1721 1464 cm$^{-1}$; $[\alpha]^{21}_D$=−4.85 (CHCl$_3$, 1.201 μmol) [Found M+Na$^+$: 911.52; C$_{50}$H$_{92}$NaO$_5$SiN$_4$S requires: 911.65].

EXAMPLE 12

Compound L was prepared as follows:

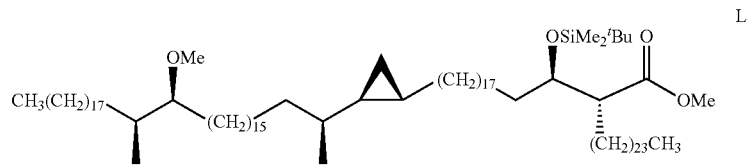

L

Lithium hexamethyldisilazide (0.2920 ml, 0.309 mmol, 1.06M) was added dropwise to a stirred solution of compound K (183 mg, 0.206 mmol) and compound F (172 mg, 0.227 mmol) in dry THF (10 ml) under nitrogen at −20° C. The temperature rose to −10° C. during the addition of the base, and a yellow solution resulted. The mixture was allowed to reach RT and was stirred for 1 hr, when TLC showed no starting material was left, then cooled to 0° C. and quenched with sat. aq. ammonium chloride (10 ml). The product was extracted with petrol/ether (1:1, 3×10 ml). The combined organic layers were washed with brine (20 ml), dried and evaporated to give an oil, which was purified by column chromatography eluting with petrol/ether (20:1) to give methyl 2-((R)-(E/Z)-1-(tert-butyldimethylsilyloxy)-19-((1S,2R)-2-((2S,18S,19S)-18-methoxy-19-methyl heptatriacontan-2-yl)cyclopropyl)nonadec-10-enyl)hexacosanoate (80.6 mg, 28%). Dipotassium azodicarboxylate (0.33 g, 1.708 mmol, 30 mol. equiv.) was added to a stirred solution of the above compound (80.6 mg, 0.057 mmol) in THF (5 ml) and methanol (5 ml) at 10° C. under nitrogen, giving a yellow precipitate. A solution of glacial acetic acid (1 ml) and THF (2 ml) was added dropwise over 48 hrs, after which a white precipitate had formed. The mixture was cooled to 0° C. and poured slowly into sat. aq. sodium hydrogen carbonate (5 ml) and then extracted with petrol/ether (1:1, 3×10 ml). The combined organic layers were washed with water (10 ml), dried and evaporated to give a thick oil which slowly solidified. The residue was purified via column chromatography eluting in petrol/ether (10:1) to give a white solid, methyl 2-((R)-1-(tert-butyldimethylsilyloxy)-19-((1S, 2R)-2-(2S,18S,19S)-18-methoxy-19-methylheptatriacontan-2-yl)cyclopropyl)nonadecyl) hexacosanoate (75.7 mg, 94%), which showed $\delta_H$ (500 MHz, CDCl$_3$): 3.92-3.90 (1H, m), 3.66 (3H, s), 3.35 (3H, s), 2.97-2.95 (1H, m), 2.54 (1H, ddd, J 3.75, 7.25, 11 Hz), 1.58-1.18 (150H, br. m including br. s at 1.27), 0.91-0.85 (21H, m), 0.48-0.44 (1H, m), 0.22-0.18 (1H, m), 0.17-0.14 (1H, m), 0.13-0.09 (1H, m), 0.05 (3H, s), 0.03 (3H, s); $\delta_C$ (125 MHz, CDCl$_3$): 175.1, 125.5, 85.5, 73.2, 65.9, 57.7, 51.6, 38.1, 37.4, 37.1, 35.8, 35.4, 34.5, 33.7, 32.8, 32.4, 31.9, 31.1, 30.5, 30.3, 30.1, 30.0, 29.9, 29.8, 29.7, 29.64, 29.60, 29.52, 29.49, 29.4, 27.8, 27.6, 27.5, 27.3, 26.2, 26.1, 25.8, 23.7, 22.7, 19.7, 18.6, 18.0, 14.9, 14.1, 10.5, −4.4, −4.9; $v_{max}$: 2923, 2852, 1741, 1465 cm$^{-1}$; $[\alpha]^{24}_D$=−1.45 (CHCl$_3$, 0.856 μmol); [Found M+Na$^+$: 1446.21; C$_{95}$H$_{190}$NaO$_4$Si requires: 1446.43].

EXAMPLE 13

Compound M, a sulfur-containing mycolic acid derivative was prepared as follows:

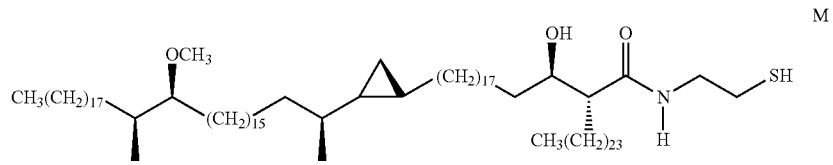

A dry polyethylene vial equipped with a rubber septum was charged with compound L (70 mg, 0.0494 mmol) in dry THF (4 ml) under nitrogen at 0° C. Pyridine (0.2 ml) and hydrogen fluoride-pyridine complex (0.2 ml, 0.140 mmol, 208 mol. equiv.) were added and the mixture stirred for 32 hrs at 43° C. When TLC analysis indicated completion of the reaction the mixture was neutralised by slowly pouring the mixture into sat. aq. sodium hydrogen carbonate (10 ml) until no more carbon dioxide was liberated. The product was extract with petrol/ether (1:1, 3×50 ml), dried and evaporated to give a white solid. This was purified via column chromatography eluting with petrol/ether (4:1) to give a white solid, methyl 2-((R)-1-hydroxy-19-((1S,2R)-2-((2S, 18S,19S)-18-methoxy-19-methylheptatriacontan-2-yl)cyclopropyl)nonadecyl) hexacosanoate (35 mg, 54%).

Lithium hydroxide monohydrate (20 mg, 0.835 mmol, 30 mol. equiv.) was added to a stirred solution of the white solid (35 mg, 0.0269 mmol) in THF (2.5 ml), methanol (0.3 ml) and water (0.3 ml) at RT. The mixture was stirred at 43° C. for 18 hrs, when TLC analysis indicated completion of the reaction, then cooled to RT and acidified with hydrochloric acid (5%, 1 ml) and the aqueous layer extracted with warm petrol/ether (1:1, 3×10 ml). The combined organic extracts were dried and evaporated, and then purified by column chromatography eluting with petrol/ethyl acetate (5:1) to give a white solid, (R)-2-((R)-1-hydroxy-19-((1S,2R)-2-((2S,18S,19S)-18-methoxy-19-methylheptatriacontan-2-yl) cyclopropyl)nonadecyl)hexacosanoic acid (24.0 mg, 69%).

This white solid (25 mg, 0.0193 mmol)) was added to a solution of N hydroxy succinimide (2.2 mg, 0.0193 mmol) in dry ethyl acetate (2 ml). A solution of DCC (4.0 mg, 0.0193 mmol) in dry ethyl acetate (1 ml) was added and the reaction mixture was stirred overnight at room temperature. DCU was removed by filtration and the filtrate was concentrated under reduced pressure. Column chromatography (petrol/ethyl acetate, 5:1) gave (2R)-2,5-dioxopyrrolidin-1-yl 2-((1R)-1-hydroxy-19-((1R)-2-((2S,19S,20S)-19-methoxy-20-methyloctatriacontan-2-yl)cyclopropyl)nonadecyl)hexacosanoate (10.3 mg, 0.0074 mmol, 38%) as a white solid. The white solid (8.3 mg, 0.00597 mmol) and 2-mercaptoethylamine hydrochloride (1.0 mg, 0.00895 mmol) were suspended in dry dichloromethane (2 ml). Triethylamine (1.8 mg, 0.0179 mmol) that was dissolved in dry dichloromethane (1 ml) was added to the solution. The reaction was allowed to heat under reflux for 3 nights and more 2-mercaptoethylamine hydrochloride (1.0 mg, 0.00895 mmol) was added. The solution was again heated under reflux for a further 3 nights. Ethyl acetate (10 ml) and ethanol (5 ml) were added to the cooled solution to form a clear solution. The organic solution was then washed with dilute acid (3×10 ml) and water (2×10 ml). The organic solution was dried, filtered and evaporated. Column chromatography (petrol/ethyl acetate, 5:1) gave (2R)-2-((1R)-1-Hydroxy-19-((1R)-2-((2S,19S,20S)-19-methoxy-20-methyloctatriacontan-2-yl)cyclopropyl)nonadecyl)-N-(2-mercaptoethyl)hexacosanamide (3.7 mg, 0.00273 mmol, 46%) as a white solid.

EXAMPLE 14

The N-hydroxysuccinimide ester of natural mycolic acid was prepared according to the following method:

Natural mycolic acid (18 mg, 0.0138 mmol) was added to a solution of N hydroxy succinimide (2 mg, 0.0138 mmol) in dry ethyl acetate (2 ml). A solution of DCC (3 mg, 0.0138 mmol) in dry ethyl acetate (1 ml) was added and the reaction mixture was stirred overnight at room temperature. DCU was removed by filtration and the filtrate was concentrated under reduced pressure. Column chromatography (petrol/ethyl acetate, 5:2) gave the N-hydroxysuccinimide ester of natural mycolic acid (11.7 mg, 0.0084 mmol, 61%) as a white solid.

EXAMPLE 15

The N-(2-mercaptoethyl)amide of natural mycolic acid was prepared according to the following method:

The N-hydroxysuccinimide ester of natural mycolic acid (11.3 mg, 0.0081 mmol) and 2-mercaptoethylamine hydrochloride (1.5 mg, 0.0121 mmol) were suspended in dry dichloromethane (2 ml). Triethylamine (2.5 mg, 3.4 μl, 0.0242 mmol) that was dissolved in dry dichloromethane (1 ml) was added to the solution. The reaction was allowed to heat under reflux for 3 nights and more 2-mercaptoethylamine hydrochloride (1.5 mg, 0.0121 mmol) was added. The solution was again heated under reflux for a further 3 nights. Ethyl acetate (15 ml) and ethanol (10 ml) were added to the cooled solution to form a clear solution. The organic solution was then washed with dilute acid (3×20 ml) and water (2×20 ml). The organic solution was dried, filtered and evaporated. Column chromatography (petrol/ethyl acetate, 5:2) gave the N-(2-mercaptoethyl)amide of natural mycolic acid (5.5 mg, 0.0040 mmol, 50%) as a white solid.

EXAMPLE 16

The method of the first aspect of the present invention in embodiments in which the antigen includes a sulfur atom in the molecule may be carried out as follows:

10 mM phosphate buffer (pH 7.4) (10 ml), colloidal gold (10 ml, 0.01% Au) and 5 μM thiolated antigen solution (2.5 ml) were put in a glass vial, and placed in a shaker overnight. 1 ml aliqouts from the aqueous layer of this solution was taken and centrifuged at 13,200 rpm for 25 minutes. The supernatant was removed and the remaining coated gold nanoparticles were re-suspended in 10 mM phosphate buffer (pH 7.4) (1 ml) before being re-combined and then transferred into the ELISA wells (180 µl/well). Sera (20 µl) (diluted to a 1 in 5,000 dilution in 10 mM phosphate buffer (pH 7.4)) was added to each well and left for 30 minutes. A saturated aqueous solution of NaCl (20 µl) was added to each well and left for 15 minutes before reading the absorbance at 540 nm, 570 nm and 630 nm.

The antigen solution is initially pink/red in colour. Upon addition of the saturated NaCl solution if the sera is positive for TB the antigen-gold complex remains in solution and no colour change is observed. If the sera is negative for TB the antigen-gold complex aggregates/precipitates from the solution and the mixture turns blue. Measuring the absorption of UV-visible light allows a quantitative assessment of the interaction to be made, i.e. the ratio of blue (negative) to red (positive) light can be measured.

EXAMPLE 17

The method of the first aspect of the present invention in embodiments in which the antigen does not include a sulfur atom in the molecule but is linked via a sulfur-containing linker compound may be carried out as follows:

10 mM phosphate buffer (pH 7.4) (10 ml), colloidal gold (10 ml, 0.01% Au) and 5 µM linker compound solution (2.5 ml) were put in a glass vial, and placed in a shaker for 16 hours. A 5 µM antigen solution (antigen dissolved in hexane) (2.5 ml) was added to this vial, and left on a shaker for a further 16 hours. 1 ml aliqouts were taken from the aqueous layer of this solution and centrifuged at 7000 RCF for 12 minutes. The supernatant was removed and the remaining coated gold nanoparticles were re-suspended in 10 mM phosphate buffer (pH 7.4) (1 ml) before being re-combined and then transferred into the ELISA wells (180 µl/well). Sera (20 µl) (diluted to a 1 in 5,000 dilution in 10 mM phosphate buffer (pH 7.4)) was added to each well and left for 30 minutes. A saturated aqueous solution of NaCl (20 µl) was added to each well and left for 15 minutes before reading the absorbance at 540 nm and 630 nm.

The antigen solution is initially red in colour. Upon addition of the saturated NaCl solution if the sera is positive for TB the antigen-gold complex remains in solution and no colour change is observed. If the sera is negative for TB the antigen-gold complex aggregates/precipitates from the solution and the mixture turns blue. Measuring the absorption of UV-visible light allows a quantitative assessment of the interaction to be made, i.e. the ratio of blue (negative) to red (positive) light can be measured.

EXAMPLE 18

Quantitative analysis assessment of the interaction when testing with a number of antigens was carried out. This was used to determine the level of aggregation/precipitation of the gold nanoparticles carrying the antigen. As described herein and with particular reference to the methods of example 16 and example 17, in the absence of an antibody to bind to the antigen, upon addition of saturated sodium chloride the antigen-coated gold nanoparticles aggregate and/or precipitate from solution. In an idealised situation in which no antibody is present there would be complete (i.e. 100%) aggregation. In an idealised situation in which all of the antigen is bonded to antibody there would be no aggregation (i.e. 0%) upon addition of the saturated sodium chloride solution.

The percentage aggregation may be calculated as follows:

$$A = \frac{\text{Absorbance at 540 nm}}{\text{Absorbance at 630 nm}}$$

$$A_0 = \frac{\text{Absorbance at 540 nm when 0\% aggregation}}{\text{Absorbance at 630 nm when 0\% aggregation}}$$

$$A_{100} = \frac{\text{Absorbance at 540 nm when 100\% aggregation}}{\text{Absorbance at 630 nm when 100\% aggregation}}$$

$$\text{Percentage Aggregation} = \frac{A_0 - A}{A_0 - A_{100}} \times 100$$

EXAMPLE 19

Compound H was used as an antigen in the method of example 16. Three sera samples known to be positive and three sera samples known to be negative were used in the method.

In each case the absorbance of the sample at 540 nm and the absorbance at 630 nm was measured. The results were used to calculate the percentage aggregation for each sample as described in example 18. The colour of the sample was also observed. The results are in table 1:

| Sample | Positive/negative | Percentage aggregation | Colour |
| --- | --- | --- | --- |
| 1 | positive | 16 | pink |
| 2 | positive | 30 | pink |
| 3 | positive | 17 | pink |
| 4 | negative | 60 | blue |
| 5 | negative | 64 | blue |
| 6 | negative | 60 | blue |

EXAMPLE 20

Sulfur-containing linker compound J was coated onto gold nanoparticles according to the method of example 17, followed by the antigen below:

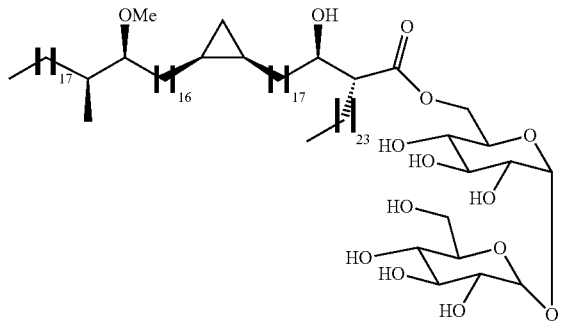 [SMILES: CC[C@H](C)[C@H](C[C@H]1C[C@H]1C[C@@H](O)[C@@H](CC)C(=O)OCC1OC(OC2OC(CO)C(O)C(O)C2O)C(O)C(O)C1O)OC]

Three sera samples known to be positive and three sera samples known to be negative were used in the method.

In each case the absorbance of the sample at 540 nm and the absorbance at 630 nm was measured. The results were used to calculate the percentage aggregation for each sample as described in example 18. The colour of the sample was also observed. The results are in table 2:

| Sample | Positive/negative | Percentage aggregation | Colour |
|---|---|---|---|
| 1 | positive | 0 | pink |
| 2 | positive | 0 | pink |
| 3 | positive | 0.16 | pink |
| 4 | negative | 77 | blue |
| 5 | negative | 71 | blue |
| 6 | negative | 54 | purple |

EXAMPLE 21

Sulfur-containing linker compound J was coated onto gold nanoparticles according to the method of example 17, followed by a commercially available antigen from Sigma comprising the trehalose dimycolate of a mixture of natural mycolic acids.

Three sera samples known to be positive and three sera samples known to be negative were used in the method.

In each case the absorbance of the sample at 540 nm and the absorbance at 630 nm was measured. The results were used to calculate the percentage aggregation for each sample as described in example 18. The colour of the sample was also observed. The results are in table 3:

| Sample | Positive/negative | Percentage aggregation | Colour |
|---|---|---|---|
| 1 | positive | 35 | pink |
| 2 | positive | 12 | pink |
| 3 | positive | 18 | pink |
| 4 | negative | 94 | blue |
| 5 | negative | 80 | blue |
| 6 | negative | 66 | purple |

EXAMPLE 22

An alternative method in which centrifugation of the gold nanoparticles before use is not carried out is described below. Similar results were obtained by this method.

10 mM phosphate buffer (pH 7.4) (10 ml), colloidal gold (10 ml, 0.01% Au) and 5 µM thiolated stearic acid solution (2.5 ml) were put in a glass vial, and placed in a shaker for 16 hours. A 5 µM antigen solution (antigen dissolved in hexane) (2.5 ml) was added to this vial, and left on a shaker for a further 16 hours. Aliquots from the aqueous layer are then transferred into the ELISA wells (180 µl/well). Sera (20 µl) (diluted to a 1 in 2,500 dilution in 10 mM phosphate buffer (pH 7.4)) was added to each well and left for 30 minutes. A saturated aqueous solution of NaCl (20 µl) was added to each well and left for 15 minutes before reading the absorbance at 540 nm and 630 nm.

EXAMPLE 23

Analysis has been carried out to determine whether the gold nanoparticle—antigen complexes retain their stability and activity over time. The complexes were tested for stability and activity after periods of 1, 2, 3 and 6 months following formation, with storage at 4° C. UV-visible spectroscopy showed the same patterns for two serum samples after storing the complexes for the time periods mentioned above as were observed immediately following formation. Thus the complexes remain stable and active and are still able to distinguish positive and negative serum samples at least 6 months after their formation.

The invention claimed is:

1. A method of determining the presence or absence in a sample of an antibody indicative of exposure to mycobacteria, the method comprising:
   (a) linking an antigen to colloidal gold to provide a gold-antigen species;
   (b) contacting the gold-antigen species with the sample to produce a suspension comprising the gold-antigen species and the sample;
   (c) adding to the suspension a diagnosis agent selected from the group consisting of: sodium chloride, magnesium chloride, and potassium chloride, wherein the addition of the diagnosis agent to the suspension produces a different coloured suspension depending on whether the sample contains or does not contain the antibody; and
   (d) observing the colour of the sample,
   wherein the antigen includes at least one mycolic acid derived antigen selected from the group consisting of:
      (i) mycolic acids obtained from natural sources;
      (ii) synthetically prepared mycolic acids;
      (iii) salts of mycolic acids;
      (iv) esters of mycolic acids (i) and/or (ii); and
      (v) sulfur-containing mycolic acids and/or salts or esters thereof.

2. The method according to claim 1, wherein the mycobacteria is *Mycobacterium tuberculosis*.

3. The method according to claim 1, wherein the antigen is linked to the colloidal gold by a gold-sulfur bond.

4. The method according to claim 3, wherein the gold-sulfur bond is formed between the colloidal gold and a sulfur atom contained within the antigen molecule.

5. The method according to claim 3, wherein the gold-sulfur bond is formed between the colloidal gold and a sulfur-containing linker compound linked to the antigen.

6. The method according to claim 1, in which step (d) involves visually observing the presence or absence of a colour change to provide a qualitative assessment.

7. The method according to claim 1, wherein step (d) involves quantitative measurement of an intensity of light absorbance at one or more wavelengths and at one or more points in time.

8. The method of claim 1, wherein the mycolic acid derived antigen is selected from the group consisting of:
   (i) mycolic acids obtained from natural sources;
   (ii) synthetically prepared mycolic acids; and
   (v) sulphur-containing mycolic acids and/or salts or esters thereof.

* * * * *

UNITED STATES PATENT AND TRADEMARK OFFICE
CERTIFICATE OF CORRECTION

PATENT NO. : 9,945,852 B2
APPLICATION NO. : 14/115929
DATED : April 17, 2018
INVENTOR(S) : Christopher David Gwenin et al.

Page 1 of 1

It is certified that error appears in the above-identified patent and that said Letters Patent is hereby corrected as shown below:

On the Title Page

The Assignee - "Arcis Biotechnology Holdings Limited, Warrington (GB)" should be changed to --Bangor University, Gwynedd (GB)--

Signed and Sealed this
Twenty-sixth Day of February, 2019

Andrei Iancu
*Director of the United States Patent and Trademark Office*